US011633421B2

(12) United States Patent
Brenner et al.

(10) Patent No.: US 11,633,421 B2
(45) Date of Patent: Apr. 25, 2023

(54) USE OF NAD PRECURSORS FOR IMPROVING MATERNAL HEALTH AND/OR OFFSPRING HEALTH

(71) Applicant: UNIVERSITY OF IOWA RESEARCH FOUNDATION, Iowa City, IA (US)

(72) Inventors: Charles M. Brenner, Iowa City, IA (US); Po Hien Ear, Iowa City, IA (US); Ankita Chadda, Iowa City, IA (US); Marie E. Migaud, Iowa City, IA (US); Hanna Stevens, Iowa City, IA (US)

(73) Assignee: UNIVERSITY OF IOWA RESEARCH FOUNDATION, Iowa City, IA (US)

(*) Notice: Subject to any disclaimer, the term of this patent is extended or adjusted under 35 U.S.C. 154(b) by 567 days.

(21) Appl. No.: 16/464,359

(22) PCT Filed: Nov. 29, 2017

(86) PCT No.: PCT/US2017/063733
§ 371 (c)(1),
(2) Date: May 28, 2019

(87) PCT Pub. No.: WO2018/102426
PCT Pub. Date: Jun. 7, 2018

(65) Prior Publication Data
US 2021/0106606 A1  Apr. 15, 2021

Related U.S. Application Data

(60) Provisional application No. 62/427,661, filed on Nov. 29, 2016.

(51) Int. Cl.
| | |
|---|---|
| A61K 31/7084 | (2006.01) |
| A61P 15/14 | (2006.01) |
| A61P 3/04 | (2006.01) |
| A61K 31/706 | (2006.01) |
| A61P 25/28 | (2006.01) |
| A61P 25/22 | (2006.01) |
| A61K 45/06 | (2006.01) |

(52) U.S. Cl.
CPC ........ *A61K 31/7084* (2013.01); *A61K 31/706* (2013.01); *A61K 45/06* (2013.01); *A61P 3/04* (2018.01); *A61P 15/14* (2018.01); *A61P 25/22* (2018.01); *A61P 25/28* (2018.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,055,460 A | 10/1991 | Friedlander |
| 6,255,291 B1 | 7/2001 | Germano |
| 6,624,150 B2 | 9/2003 | Yerxa et al. |
| 6,867,231 B1 | 3/2005 | Burke et al. |
| 7,022,680 B2 | 4/2006 | Sauve et al. |
| 7,138,122 B2 | 11/2006 | Burke et al. |
| 7,179,791 B2 | 2/2007 | Stamler et al. |
| 7,544,497 B2 | 6/2009 | Sinclair et al. |
| 7,601,332 B2 | 10/2009 | Vlahov et al. |
| 7,615,535 B2 | 11/2009 | Stamler et al. |
| 7,776,326 B2 | 8/2010 | Milbrandt et al. |
| 7,977,049 B2 | 7/2011 | Sinclair et al. |
| 8,105,568 B2 | 1/2012 | Vlahov et al. |
| 8,106,184 B2 | 1/2012 | Sauve et al. |
| 8,114,626 B2 | 2/2012 | Brenner et al. |
| 8,197,807 B2 | 6/2012 | Brenner |
| 8,217,006 B2 | 7/2012 | Stamler et al. |
| 8,383,086 B2 | 2/2013 | Brenner |
| 9,000,147 B2 | 4/2015 | Sauve et al. |
| 9,321,797 B2 | 4/2016 | Sauve et al. |
| 9,408,834 B2 | 8/2016 | Zemel et al. |
| 2002/0128205 A1 | 9/2002 | Stamler et al. |
| 2004/0224918 A1 | 11/2004 | Yatvin et al. |
| 2005/0227327 A1 | 10/2005 | Brenner |
| 2006/0025337 A1 | 2/2006 | Sinclair et al. |
| 2006/0111435 A1 | 5/2006 | Sinclair et al. |

(Continued)

FOREIGN PATENT DOCUMENTS

| | | |
|---|---|---|
| CH | 318073 A | 12/1956 |
| EP | 2805719 A1 | 11/2014 |

(Continued)

OTHER PUBLICATIONS

Shan, N , et al., "Mechanochemistry and co-crystal formation: effect of solvent on reaction kinetics", Chem Commun, 2372-2373 (2002).
Surjana, D , et al., "Role of Nicotinamide in DNA Damage, Mutagenesis, and DNA Repair", Journal of Nucleic Acids, doi:10.4061/2010/157591, 13 pages (2010).
Tanimori, S , et al., "An Efficient Chemical Synthesis of Nicotinamide Riboside (NAR) and Analogues", Bioorganic & Medicinal Chemistry Letters 12, 1135-1137 (2002).
Thiry, J , et al., "A review of pharmaceutical extrusion: Critical process parameters and scaling-up", International Journal of Pharmaceutics 479, 227-240 (2015).
Thong, H , et al., "Percutaneous penetration enhancers: an overview", Skin Pharmacol Physiol 20(6), 272-282 (2007).
Trammell, S , et al., "Nicotinamide Riboside Is a Major NAD+ Precursor Vitamin in Cow Milk 1-3", Journal of Nutrition 146(5), 957-963 (2016).

(Continued)

*Primary Examiner* — Layla D Berry
(74) *Attorney, Agent, or Firm* — Viksnins Harris Padys Malen LLP

(57) ABSTRACT

Certain embodiments of the invention provide a method for improving maternal and/or offspring health, comprising administering an effective amount of a nicotinamide adenine dinucleotide (NAD) precursor to a female mammal (e.g., pregnant or lactating female mammal).

16 Claims, 30 Drawing Sheets

(56) References Cited

U.S. PATENT DOCUMENTS

| | | | |
|---|---|---|---|
| 2006/0229265 | A1 | 10/2006 | Milburn et al. |
| 2007/0117765 | A1 | 5/2007 | Sauve et al. |
| 2008/0194803 | A1 | 8/2008 | Sinclair et al. |
| 2008/0318892 | A1 | 12/2008 | Pickering et al. |
| 2009/0069444 | A1 | 3/2009 | Joseph et al. |
| 2009/0196942 | A1 | 8/2009 | Goyarts et al. |
| 2009/0270503 | A1 | 10/2009 | Hermelin et al. |
| 2012/0108535 | A1 | 5/2012 | Sauve et al. |
| 2012/0172584 | A1 | 7/2012 | Sauve et al. |
| 2012/0251463 | A1 | 10/2012 | Brenner |
| 2012/0328526 | A1 | 12/2012 | Kristian |
| 2012/0329748 | A1 | 12/2012 | Sauve et al. |
| 2013/0011377 | A1 | 1/2013 | Perrin et al. |
| 2013/0059384 | A1* | 3/2013 | Tilly .............. A61K 31/352 435/408 |
| 2013/0165398 | A1 | 6/2013 | Huber |
| 2014/0113928 | A1 | 4/2014 | Albaghdadi et al. |
| 2015/0056274 | A1 | 2/2015 | Zemel et al. |
| 2015/0175645 | A1 | 6/2015 | Milburn et al. |
| 2016/0000745 | A1 | 1/2016 | Gojon-Zorrilla et al. |
| 2016/0250241 | A1 | 9/2016 | Deren-Lewis et al. |
| 2016/0272668 | A1 | 9/2016 | Dellinger et al. |
| 2016/0355539 | A1 | 12/2016 | Migaud et al. |
| 2017/0267709 | A1 | 9/2017 | Migaud et al. |
| 2017/0304338 | A1 | 10/2017 | Dellinger et al. |
| 2018/0147225 | A1 | 5/2018 | Brenner et al. |

FOREIGN PATENT DOCUMENTS

| | | |
|---|---|---|
| GB | 2542881 A | 4/2017 |
| KR | 101604212 B1 | 3/2016 |
| WO | 2003093290 A2 | 11/2003 |
| WO | 2006116322 A2 | 11/2006 |
| WO | 2013002880 A1 | 1/2013 |
| WO | 2013045538 A1 | 4/2013 |
| WO | 2014011676 A1 | 1/2014 |
| WO | 2014014828 A1 | 1/2014 |
| WO | 2014059031 A2 | 4/2014 |
| WO | 2015014722 A1 | 2/2015 |
| WO | 2015016829 A1 | 2/2015 |
| WO | 2015066382 A1 | 5/2015 |
| WO | 2015186068 A1 | 12/2015 |
| WO | 2015186114 A1 | 12/2015 |
| WO | 2016014927 A2 | 1/2016 |
| WO | 2016049236 A1 | 3/2016 |
| WO | 2016111992 A1 | 7/2016 |
| WO | 2016144660 A1 | 9/2016 |
| WO | 2016149277 A1 | 9/2016 |
| WO | 2017181102 A1 | 10/2017 |
| WO | 2018102426 A1 | 6/2018 |
| WO | 2018200357 A1 | 11/2018 |
| WO | 2019006262 A1 | 1/2019 |

OTHER PUBLICATIONS

Trammell, S , "Nicotinamide riboside is uniquely and orally bioavailable in mice and humans", Nature Comm 7, 12948, 14 pages (2016).
Trammell, S , "Nicotinamide Riboside Opposes Type 2 Diabetes and Neuropathy in Mice", Scientific Reports 6, 2693, 7 pages (2016).
Trask, A , et al., "Achieving Polymorphic and Stoichiometric Diversity in Cocrystal Formation: Importance of Solid-State Grinding, Powder X-ray Structure Determination, and Seeding", Crystal Growth & Design 5(6), 2233-2241 (2005).
Trask, A, et al., "Screening for crystalline salts via mechanochemistry", Chem Commun 51-53 (2006).
Urberg, M , et al., "Evidence for Synergism Between Chromium and Nicotinic Acid in the Control of Glucose Tolerance in Elderly Humans", Metabolism 36(9), 896-899 (1987).
Verhoeven, E , et al., "Influence of formulation and process parameters on the release characteristics of ethylcellulose sustained-release mini-matrices produced by hot-melt extrusion", European Journal of Pharmaceutics and Biopharmaceutics 69, 312-319 (2008).
Verhoeven, E , et al., "Xanthan gum to tailor drug release of sustained-release ethylcellulose mini-matrices prepared via hot-melt extrusion: in vitro and in vivo evaluation", European Journal of Pharmaceutics and Biopharmaceutics 63, 320-330 (2006).
Wahl, P , et al., "Inline monitoring and a PAT strategy for pharmaceutical hotmelt extrusion", International Journal of Pharmaceutics 455, 159-168 (2013).
Xu, P , et al., "Vitamin B3, the nicotinamide adenine dinucleotides and aging", Mechanisms of Ageing and Development 131, 287-298 (2010).
Yoshikawa, M , et al., "Studies of Phosphorylation. III. Selective Phosphorylation of Unprotected Nucleosides", Bulletin of the Chemical Society of Japan 42, 3505-3508 (1969).
Yuvaraj, S , et al., "Effect of Coenzyme Q10, Riboflavin and Niacin on Tamoxifen treated postmenopausal breast cancer women with special reference to blood chemistry profiles", Breast Cancer Res Treat 114, 377-384 (2009).
Almeida, A , et al., "Upscaling and in-line process monitoring via spectroscopic techniques of ethylene vinyl acetate hot-melt extruded formulations", International Journal of Pharmaceutics 439, 223-229 (2012).
Ansel , "Section IV Semisolid Dosage Forms and Transdermal Systems", Pharmaceutical Dosage Forms Drug Delivery Systems 9th Ed, Chapter 10, 22 pages (2011).
Applegate, L , et al., "Identification of the Molecular Target for the Suppression of Contact Hypersensitivity", J Exp Med 170, 1117-1131 (1989).
Baker, H , et al., "Vitamin profile of 563 gravidas during trimesters of pregnancy", J Am Coll Nutr 21(1), 33-37 (2002).
Berge, S. , et al., "Pharmaceutical Salts", Journal of Pharmaceutical Sciences, vol. 66, No. 1, 1-19 (1977).
Bieganowski, P , et al., "Discoveries of Nicotinamide Riboside as a Nutrient and Conserved NRK Genes Establish a Preiss-Handler Independent Route to NAD+ in Fungi and Humans", Cell 117(4), 495-502 (2004).
Biospace , "ChromaDex, Inc. Initiates First Human Clinical Study to Confirm ChromaDex's Niagen TM Nicotinamide Riboside Will Increase NAD+", http://www.biospace.com/News/chromadex-inc-initiates-first-human-clinical-study/339980, 6 pages (2014).
Bogan, K , et al., "Nicotinic Acid, Nicotinamide, and Nicotinamide Riboside: A Molecular Evaluation of NAD+ Precursor Vitamins in Human Nutrition", Annual Review of Nutrition 28(1), 115-130 (2008).
Breitenbach, J , "Melt extrusion: from process to drug delivery technology", European Journal of Pharmaceutics and Biopharmaceutics 54, 107-117 (2002).
Bruce, L , et al., "Properties of hot-melt extruded tablet formulations for the colonic delivery of 5-aminosalicylic acid", European Journal of Pharmaceutics and Biopharmaceutics 59, 85-97 (2005).
Bzowska, A , et al., "Purine nucleoside phosphorylases: properties, functions, and clinical aspects", Pharmacology & Therapeutics 88, 249-425 (2000).
Canto, C , et al., "Crosstalk between poly(ADP-ribose) polymerase and sirtuin enzymes", Molecular Aspects of Medicine 34, 1168-1201 (2013).
Chromadex , Press Releases, 3 pages (May 29, 2013).
Conze, D , et al., "Safety assessment of nicotinamide riboside, a form of vitamin B3", Hum Exp Toxicol 35(11), 1149-1160 (2016).
Crossey, K , et al., "Exploiting the use of ionic liquids to access phosphorodiamidites", RSC Advances 2, 2988-2993 (2012).
Crossey, K , et al., "Nucleoside phosphitylation using ionic liquid stabilised phosphorodiamidites and mechanochemistry", Chem Commun 48, 11969-11971 (2012).
Crowley, M , et al., "Pharmaceutical Applications of Hot-Melt Extrusion: Part I", Drug Development and Industrial Pharmacy 33, 909-926 (2007).
Ear, P , et al., "Maternal Nicotinamide Riboside Enhances Postpartum Weight Loss, Juvenile Offspring Development, and Neurogenesis of Adult Offspring", Cell Reports 26, 969-983 (2019).
Friedlos, F , et al., "Metabolism of nad(p)h by blood components: Relevance to bioreductively activated prodrugs in a targeted enzyme therapy system", Biochem Pharmacol 44(4), 631-635 (1992).

(56) References Cited

OTHER PUBLICATIONS

Gong, B , et al., "Nicotinamide riboside restores cognition through an upregulation of proliferator-activated receptor-g coactivator 1a regulated b-secretase 1 degradation and mitochondrial gene expression in Alzheimer's mouse models", Neurobiology of Aging 34, 1581-1588 (2013).
Haratake, A , et al., "UVB-Induced Alterations in Permeability Barrier Function: Roles for Epidermal Hyperproliferation and Thymocyte-Mediated Response", J Invest Dermatol 108, 769-775 (1997).
Hardacre, C , et al., "Overcoming hydrolytic sensitivity and low solubility of phosphitylation reagents by combining ionic liquids with mechanochemistry", Chem Commun 47, 5846-5848 (2011).
Hasa, D , et al., "Cocrystal Formation through Mechanochemistry: from Neat and Liquid-Assisted Grinding to Polymer-Assisted Grinding", Angew Chem Int Ed 54, 7371-7375 (2015).
Haynes, H , et al., "Codehydrogenases. Part II. A Synthesis of Nicotinamide Nucleotide", J Med Chem Soc, 3727-3732 (1957).
Hughey, J , et al., "The use of inorganic salts to improve the dissolution characteristics of tablets containing Soluplus®-based solid dispersions", European Journal of Pharmaceutical Sciences 48, 758-766 (2013).
Janssens, S , et al., "The use of a new hydrophilic polymer, Kollicoat IR®, in the formulation of solid dispersions of Itraconazole", European Journal of Pharmaceutical Sciences 30, 288-294 (2007).
Jarman, M , et al., "4-Substituted nicotinic acids and nicotinamides. Part III. Preparation of 4-methylnicotinic acid riboside", J Chem Soc (C), 918-920 (1969).
Jiang, S , et al., "Ultraviolet B-induced alterations of the skin barrier and epidermal calcium gradient", Exp Dermatol 16(12), 985-992 (2007).
Kahn, N , et al., "Effective treatment of mitochondrial myopathy by nicotinamide riboside, a vitamin B3", EMBO Mol Med 6(6), 721-731 (2014).
Karki, S , et al., "Screening for Pharmaceutical Cocrystal Hydrates via Neat and Liquid-Assisted Grinding", Molecular Pharmaceutics 4(3), 347-354 (2007).
Krier, F , et al., "PAT tools for the control of co-extrusion implants manufacturingprocess", International Journal of Pharmaceutics 458, 15-24 (2013).
Kulikova, V , et al., "Generation, Release, and Uptake of the NAD Precursor Nicotinic Acid Riboside by Human Cells", Journal of Biological Chemistry 290(45), 27124-27137 (2015).
Lee, J , et al., "A chemical synthesis of nicotinamide adenine dinucleotide (NAD+)", Chem Commun 729-730 (1999).
Liu, H , et al., "Effects of Screw Configuration on Indomethacin Dissolution Behavior in Eudragit E PO", Advances in Polymer Technology 31(4), 331-342 (2012).
Maniruzzaman, M , et al., "A Review of Hot-Melt Extrusion: Process Technology to Pharmaceutical Products", International Scholarly Research Network Pharmaceutics, Article ID 436763, 9 pages (2012).
Mikhailopulo, I , "Synthesis of Glycosides of Nicotinamide and Nicotinamide Mononucleotide", Synthesis 388-389 (1981).
Miller, D , et al., "Targeted Intestinal Delivery of Supersaturated Itraconazole for Improved Oral Absorption", Pharm Res 25, 1450, 32 pages (2008).
Nakamichi, K , et al., "The role of the kneading paddle and the effects of screw revolution speed and water content on the preparation of solid dispersions using a twin-screw extruder", International Journal of Pharmaceutics 241, 203-211 (2002).
Oba, C , et al., "Collagen hydrolysate intake improves the loss of epidermal barrier function and skin elasticity induced by UVB irradiation in hairless mice", Photodermatol Photoimmunol Photomed 29(4), 204-211 (2013).
Pankiewicz, K , "Novel Nicotinamide Adenine Dinucleotide Analogues as Potential Anticancer Agents: Quest for Specific Inhibition of Inosine Monophosphate Dehydrogenase", Pharmacol Ther 76, 1-3, 89-100 (1997).
Patent Cooperation Treaty , International Searching Authority, Search Report and Written Opinion for PCT/US2017/06733, 15 pages, dated Feb. 27, 2018.
Paudel, K , et al., "Challenges and opportunities in dermal/transdermal delivery", Ther Deliv 1(1), 109-131 (2010).
Plasman, V , "Triterpene Saponins, Quaternary Ammonium Compounds, Phosphatidyl Cholines, and Amino Acids in the Pronotal and Elytral Secretions of Platyphora opima and Desmogramma subtropica", J Nat Prod 63, 1261-1264 (2000).
Ravalico, F , et al., "Rapid synthesis of nucleotide pyrophosphate linkages in a ball mill", Organic & Biomolecular Chemistry 9, 6496-6497 (2011).
Redpath, P , et al., "INettiercotinamide Benzimidazolide Dinucleotides, Non-Cyclisable Analogues of NAD+", Synlett 25, 2331-2336 (2014).
Reitz, E , et al., "Residence time modeling of hot melt extrusion processes", European Journal of Pharmaceutics and Biopharmaceutics 85, 1200-1205 (2013).
Repka, M , et al., "Pharmaceutical Applications of Hot-Melt Extrusion: Part II", Drug Development and Industrial Pharmacy 33, 1043-1057 (2007).
Romanski, F , et al., "The Importance of Monitoring Process Parameters as a Method for Quality Control for Hot Melt Extrusion", BASF Corp, 1 page (2013).
Sarode, A , et al., "Hot melt extrusion (HME) for amorphous solid dispersions: Predictive tools for processing and impact of drug-polymer interactions on supersaturation", European Journal of Pharmaceutical Sciences 48, 371-384 (2013).
Shah, S , et al., "Melt extrusion with poorly soluble drugs", International Journal of Pharmaceutics 453, 233-252 (2013).
Jaster, E , et al., "Supplemental Nicotinic Acid or Nicotinamide for Lactating Dairy Cows", Journal of Dairy Science 73(10), 2880-2887 (1990).

\* cited by examiner

Milk collection

USE OF NAD PRECURSORS FOR IMPROVING MATERNAL HEALTH AND/OR OFFSPRING HEALTH

RELATED APPLICATION

This application claims the benefit of priority of U.S. Provisional Application Ser. No. 62/427,661 filed on Nov. 29, 2016, which application is incorporated by reference herein.

BACKGROUND OF THE INVENTION

There are many challenges associated with maintaining proper maternal health during and after pregnancy. For example, mothers often have difficulties losing unwanted weight gained during pregnancy, sustaining sufficient milk production to feed newborns effectively and time-efficiently, and maintaining a suitable niacin status (Baker et al., *J. Am. Coll. Nutr.* 2002 Feb;21(1):33-7). Additionally, neonatal and child health and brain development are often limited by the availability of mother's milk, and the body composition, hypoglycemia and lack of mobility of neonates and young children. However, current methods and treatments for addressing these challenges are limited.

Thus, there is a need for new methods and therapies for improving maternal health and/or offspring health (e.g., neonatal, early childhood and/or adult health).

SUMMARY OF THE INVENTION

Accordingly, certain embodiments of the invention provide a method for imparting a health benefit to a female mammal in need thereof and/or to the offspring of the female mammal, comprising administering an effective amount of a nicotinamide adenine dinucleotide (NAD) precursor to the female mammal;

wherein the health benefit imparted to the female mammal is a reduction in pregnancy associated weight gain, promotion of post-pregnancy weight loss and/or increased milk production when lactating; and wherein the health benefit imparted to the offspring is improved metabolism, improved glycemic control, increased brain mass, increased physical activity, improved development, improved physical abilities, protection against age-induced weight gain and/or reduced anxiety.

Certain embodiments of the invention provide a NAD precursor for imparting a health benefit to a female mammal in need thereof and/or to the offspring of the female mammal;

wherein the health benefit imparted to the female mammal is a reduction in pregnancy associated weight gain, promotion of post-pregnancy weight loss and/or increased milk production when the female mammal is lactating; and wherein the health benefit imparted to the offspring is improved metabolism, improved glycemic control, increased brain mass, increased physical activity, improved development, improved physical abilities, protection against age-induced weight gain and/or reduced anxiety.

Certain embodiments of the invention also provide the use of a NAD precursor to prepare a medicament useful for imparting a health benefit to a female mammal in need thereof and/or to the offspring of the female mammal;

wherein the health benefit imparted to the female mammal is a reduction in pregnancy associated weight gain, promotion of post-pregnancy weight loss and/or increased milk production when the female mammal is lactating; and wherein the health benefit imparted to the offspring is improved metabolism, improved glycemic control, increased brain mass, increased physical activity, improved development, improved physical abilities, protection against age-induced weight gain and/or reduced anxiety.

Certain embodiments of the invention provide a composition (e.g., a pharmaceutical composition) comprising a NAD precursor and an acceptable carrier (e.g., a pharmaceutically acceptable carrier) for use in imparting a health benefit to a female mammal in need thereof and/or the offspring of the female mammal, wherein the health benefit imparted to the female mammal is a reduction in pregnancy associated weight gain, promotion of post-pregnancy weight loss and/or increased milk production when the female mammal is lactating; and wherein the health benefit imparted to the offspring is improved metabolism, improved glycemic control, increased brain mass, increased physical activity, improved development, improved physical abilities, protection against age-induced weight gain and/or reduced anxiety.

Certain embodiments of the invention also provide a kit comprising a NAD precursor and instructions for administering the NAD precursor to a female mammal in need thereof for imparting a health benefit to the female mammal and/or the offspring of the female mammal, wherein the health benefit imparted to the female mammal is a reduction in pregnancy associated weight gain, promotion of post-pregnancy weight loss and/or increased milk production when the female mammal is lactating; and wherein the health benefit imparted to the offspring is improved metabolism, improved glycemic control, increased brain mass, increased physical activity, improved development, improved physical abilities, protection against age-induced weight gain and/or reduced anxiety.

Certain embodiments of the invention provide a kit comprising 1) a composition (e.g., a pharmaceutical composition) comprising a NAD precursor and a carrier, wherein the composition is formulated for oral administration; and 2) instructions for orally administering the NAD precursor to a female mammal for imparting a health benefit to the female mammal and/or the offspring of the female mammal, wherein the health benefit imparted to the female mammal is a reduction in pregnancy associated weight gain, promotion of post-pregnancy weight loss and/or increased milk production when the female mammal is lactating; and wherein the health benefit imparted to the offspring is improved metabolism, improved glycemic control, increased brain mass, increased physical activity, improved development, improved physical abilities, protection against age-induced weight gain and/or reduced anxiety.

Certain embodiments of the invention also provide a method, compound, composition or kit as described herein.

BRIEF DESCRIPTION OF THE FIGURES

FIG. 18C-D. Lactation seems to depress levels of NR (FIG. 11C) and Nam (FIG. 11D) in the liver. NR supplementation depresses the accumulation of these metabolites in the liver even more. These data suggest that the liver may be working to mobilize NR and Nam to other tissues, like the mammary.

FIG. 12A. NR promotes expression of NAD biosynthetic genes in the mammary glands. FIG. 12B. Lactating mammary gland has higher NAD+ levels and NR supplementation tends to further increase NAD+ levels. FIG. 12C. Lactation boosts NMN in mammary. FIG. 12D. Lactation and NR boost mammary NR in an additive manner.

FIG. 13A. Prolactin levels in plasma from dam on NC or NR chow. FIG. 13B. mTOR pathway is activated in NR-supplemented mammary tissue. FIG. 13C. Genes involved in lipid biosynthesis are activated in NR-supplemented mammary tissue. FIG. 13D. Genes involved in lactose synthesis pathway are activated in NR-supplemented mammary tissue.

DETAILED DESCRIPTION

Figure 1:
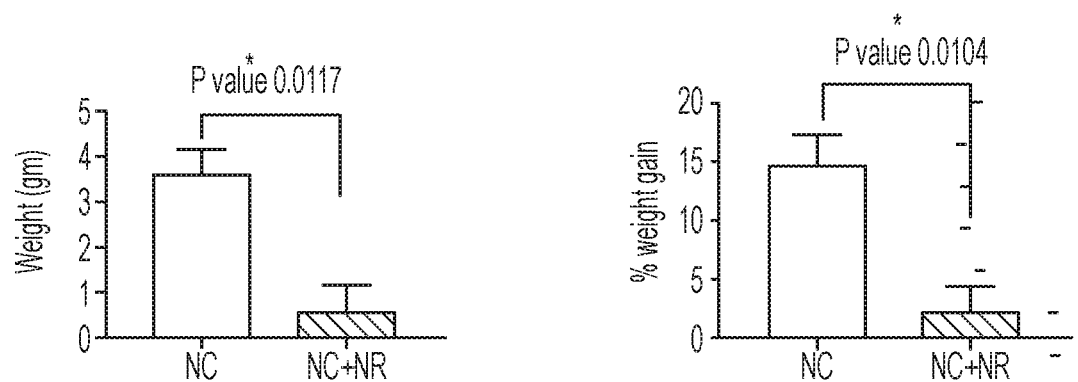
FIG. 1. Weight gain (gm) from mating to end of lactation (left panel) and percent weight gain from mating to end of lactation (right panel) in female mice fed NC or NC+nicotinamide riboside (NR).

Certain embodiments of the invention provide the use of NAD precursors, such as nicotinamide riboside (NR) and derivatives and analogs thereof, for improving maternal health and the health of offspring (e.g, neonatal and early childhood health, as well as adult health). As described herein, a number of benefits of administering NAD precursors during and after pregnancy were surprisingly discovered (see, e.g., the Examples). For example, a near total elimination of weight gain over the gestational and post-gestational interval was unexpectedly observed in pregnant/lactating mice administered NR. Additionally, a significant increase in the amount of milk produced by lactating females was observed. it was also surprisingly found that benefits of administering NR to pregnant/lactating mice were passed onto the offspring. For example, the following benefits to neonatal health were observed from the maternal administration of NR: 1) larger mass of neonates at the time of weaning; 2) larger brain mass of neonates at the time of weaning; 3) greater physical activity of neonates; and 4) correction of neonatal glycemic control from a slightly low level to an ideal level, Accordingly, an NAD precursor may be administered to a pregnant or lactating female mammal for, e.g., gestational and post-gestational weight management, to improve metabolic fitness during and post-pregnancy, to enhance lactation, to improve infant nutrition, to improve infant body composition and/or glycemic control, and/or to improve brain development, physical activity, cognitive and/or behavioral functions of offspring (e.g., babies). As described herein, an NAD precursor may also be administered to a pregnant or lactating female mammal to provide certain benefits to an offspring later in life (e.g., as an adult, despite cessation of consuming its mother's milk) (see, e.g., the Examples).

Administration of an NAD precursor to a female mammal (e.g., a reproductively active female, a pregnant female or a nursing female) may improve maternal health and/or offspring health (es., neonatal, early-childhood and/or adult health) through multiple mechanisms, including, e.g., 1) decreased maternal adiposity and improved neonatal/child metabolism with some of the maternal benefit deriving from increased transmission of high quality calories from mother to baby; 2) increased milk volume and feeding efficiency, decreasing a baby's stress during feeding time; 3) increased milk quality as evidenced by increased content of bioactive molecules such as brain derived neurotrophic factor, 4) reduced feeding time to satisfy the nutritional needs of a baby/improved mother-child bonding opportunities; 5) reduced emotional stress for mothers, who are better able to meet the nutritional needs of their baby; 6) freedom. from neonatal hypoglycemia-associated sequelae, including jitteriness, cyanosis, apnea, hypothermia, poor body tone, poor feeding, lethargy and seizures; and/or 7) improved physical activity, cognitive and behavioral functions of offspring (e.g., babies).

Methods of the Invention

Accordingly, certain embodiments of the invention provide method for imparting a health benefit to a female mammal in need thereof and/or to the offspring of the female mammal (e.g., in need thereof), comprising administering an effective amount of a nicotinamide adenine dinucleotide (NAD) precursor to the female mammal;
wherein the health benefit imparted to the female mammal is a reduction in pregnancy associated weight gain, promotion of post-pregnancy weight loss, increased milk production when lactating and/or increased milk quality; and
wherein the health benefit imparted to the offspring is improved metabolism, improved glycemic control, increased brain mass, increased physical activity, improved development, improved physical abilities, protection against age-induced weight gain and/or reduced anxiety.

In certain embodiments, the health benefit is imparted to the female mammal. In certain embodiments, the NAD precursor is administered to the female mammal pre-pregnancy, during pregnancy and/or post-pregnancy. In certain embodiments, the NAD precursor is administered to the female mammal pre-pregnancy. In certain embodiments, the NAD precursor is administered to the female mammal during pregnancy. In certain embodiments, the NAD precursor is administered to the female mammal post-pregnancy. In certain embodiments, the NAD precursor is administered to the female mammal during pregnancy and post-pregnancy. In certain embodiments, the NAD precursor is administered to the female mammal pre-pregnancy, during pregnancy and post-pregnancy.

In certain embodiments, the health benefit is a reduction in pregnancy associated weight gain. Thus, certain embodiments of the invention provide a method for reducing pregnancy associated weight gain in a female mammal (e.g., a human) in need thereof, comprising administering an effective amount of a nicotinamide adenine dinucleotide (NAD) precursor to the female mammal. In certain embodiments, pregnancy associated weight gain is reduced by at least about 10%, 20%, 30%, 40%, 50%, 60%, 70%, 80%, 90%, 95% or more (e.g., as compared to a control, such as to the amount of weight gained during pregnancy by a female mammal not administered an NAD precursor). In certain embodiments, pregnancy associated weight gain is prevented (i.e., the mother's weight returns to her pre-pregnancy weight after giving birth).

As used herein, the term "in need thereof" refers to any mammal wanting/desiring to practice a method described herein for any purpose (e.g., for medical reasons or otherwise).

As used herein, the term "pregnancy associated weight gain" refers to weight gained by a female mammal during pregnancy, excluding the weight of the offspring, amniotic fluid and other tissues/fluids expelled upon giving birth. Accordingly, "pregnancy associated weight gain" may be calculated by subtracting a female mammal's weight after giving birth (e.g., within 1 day, 1 week, 2 weeks, 1 month of giving birth, etc.) from the female mammal's pre-pregnancy weight.

In certain embodiments, the health benefit is promotion of post-pregnancy weight loss. Thus, certain embodiments of the invention provide a method for promoting post-pregnancy weight loss in a female mammal (e.g., a human) in need thereof, comprising administering an effective amount of a nicotinamide adenine dinucleotide (NAD) precursor to the female mammal. In certain embodiments, weight loss is increased by at least about 10%, 20%, 30%, 40%, 50%, 60%, 70%, 80%, 90%, 95% or more (e.g., as compared to a control, such as to the amount of weight lost by a female mammal not administered an NAD precursor). In certain embodiments, milk production and/or mammary gland development is increased in the female mammal. In certain embodiments, the female mammal loses fat and maintains lean mass.

As used herein, the terms "post-pregnancy weight loss" refers to weight loss after giving birth (e.g., 1 day, 1 week, 2 weeks, 1 month, 2 months, 3 months, 4 months, 5 months, 6 months, 7 months, 8 months, 9 months, 10 months, 11 months, 1 year, etc. after giving birth).

In certain embodiments, the health benefit is increased milk production. Thus, certain embodiments of the invention provide a method for increasing milk production in a lactating female mammal in need thereof, comprising administering an effective amount of a nicotinamide adenine dinucleotide (NAD) precursor to the female mammal. In certain embodiments, milk production is increased by at least about 10%, 20%, 30%, 40%, 50%, 60%, 70%, 80%, 90%, 95% or more (e.g., as compared to a control, such as to the milk production prior to administration). Milk production may be measured using techniques known in the art, for example using a method as described in the examples, such as measuring the volume of collected milk.

In certain embodiments, the health benefit is an improvement in the quality of the milk. As used herein, the term "milk quality" refers to the level of nutrients and vitamins present in the milk. Thus, milk having improved quality may comprise increased levels of certain nutrients and/or vitamins (e.g., brain-derived neurotrophic factor (BDNF), see also, nutrients described in the Examples). Thus, certain embodiments of the invention provide a method for increasing the quality of milk from a lactating female mammal in need thereof, comprising administering an effective amount of a nicotinamide adenine dinucleotide (NAD) precursor to the female mammal. In certain embodiments, the milk comprises increased levels of BDNF. In certain embodiments, BDNF levels are increased by at least about 10%, 20%, 30%, 40%, 50%, 60%, 70%, 80%, 90%, 95% or more (e.g., as compared to a control, such as to the BDNF levels in milk from the female mammal prior to administration).

As discussed above, the maternal administration of a NAD precursor can result in a number of benefits being passed on to offspring. These benefits may be derived in utero, a NAD precursor is administered to the mother during pregnancy) and/or through ingesting milk from the mother (i.e.. a NAD precursor is administered to a lactating mother). These benefits may be observed at the neonatal, adolescent and/or adult stages (e.g., throughout the life of the offspring, despite cessation of consuming milk from its mother).

Thus, in certain embodiments, the health benefit is imparted to the offspring of the female mammal (via maternal administration). In certain embodiments, an effective amount of the NAD precursor is administered to the female mammal while pregnant, thereby imparting the health benefit to the later born offspring. In certain embodiments, an effective amount of the NAD precursor is administered to the female mammal while lactating, wherein the offspring ingests milk from the lactating female mammal, thereby imparting the health benefit to the offspring.

In certain embodiments, the health benefit results when the offspring is a baby (e.g., for a human, e.g., less than 3 years of age). In certain embodiments, the health benefit results when the offspring is a child or adolescent (e.g., for a human, e.g., between ages 3 to 17). In certain embodiments, the health benefit results when the offspring is an adult (e.g., for a human, e.g., 18 years of age or older). In certain embodiments, the health benefit results throughout the life of the offspring.

In certain embodiments, the health benefit is improved metabolism in the offspring. Thus, certain embodiments of the invention provide a method for improving metabolism in the offspring of a female mammal, comprising 1) administering an effective amount of a nicotinamide adenine dinucleotide (NAD) precursor to a pregnant female mammal, thereby improving metabolism in the later born offspring; and/or 2) administering an effective amount of a nicotinamide adenine dinucleotide (NAD) precursor to a lactating female mammal, wherein the offspring ingests milk from the lactating female mammal, thereby improving metabolism in the offspring. In certain embodiments, the method comprises administering an effective amount of a nicotinamide adenine dinucleotide (NAD) precursor to a pregnant female mammal, thereby causing improved metabolism in the later born offspring. In certain embodiments, the method comprises administering an effective amount of a nicotinamide adenine dinucleotide (NAD) precursor to a lactating female mammal, wherein the offspring ingests milk from the lactating female mammal, thereby improving metabolism in the offspring (e.g., as compared to the metabolism of offspring from a mother not administered an NAD precursor). Methods of measuring metabolism are known in the art, for example, using an assay described herein. In certain embodiments, the improved metabolism is experienced when the offspring is an adult. In certain embodiments, the improved metabolism is experienced throughout the life of the offspring. In certain embodiments, the improved metabolism is experienced when the offspring is a baby. Thus, certain embodiments of the invention also provide a method for improving metabolism in a mammalian baby, comprising 1) administering an effective amount of a nicotinamide adenine dinucleotide (NAD) precursor to a pregnant female mammal, thereby improving metabolism in the later born mammalian baby; and/or 2) administering an effective amount of a nicotinamide adenine dinucleotide (NAD) precursor to a lactating female mammal, wherein the mammalian baby ingests milk from the lactating female mammal, thereby improving metabolism in the mammalian baby. In certain embodiments, the method comprises administering an effective amount of a nicotinamide adenine dinucleotide (NAD) precursor to a pregnant female mammal, thereby causing improved metabolism in the later born mammalian baby. In certain embodiments, the method comprises administering an effective amount of a nicotinamide adenine dinucleotide (NAD) precursor to a lactating female mammal, wherein the mammalian baby ingests milk from the lactating female mammal, thereby causing improving metabolism in the mammalian baby (e.g., as compared to the metabolism of a baby from a mother not administered an NAD precursor). In certain embodiments, the mammalian baby has improved glycemic control. In certain embodiments, the mammalian baby has an increased storage of glycogen.

As used herein, the term "baby" refers to an infant or young child. In certain embodiments, the baby is an infant or young child that ingests milk from its mother. In certain embodiments, the baby is less than 3 years of age (e.g., less than 2 years of age, less than 18 months, less than 1 year, less than 6 months, etc.).

In certain embodiments, the health benefit is improved glycemic control. Thus, certain embodiments of the invention provide a method for improving glycemic control in the offspring of a female mammal, comprising 1) administering an effective amount of a nicotinamide adenine dinucleotide (NAD) precursor to a pregnant female mammal, thereby causing improved glycemic control in the later born offspring; and/or 2) administering an effective amount of a nicotinamide adenine dinucleotide (NAD) precursor to a lactating female mammal, wherein the offspring ingests milk from the lactating female mammal, thereby causing improved glycemic control in the offspring. In certain embodiments, the method comprises administering an effective amount of a nicotinamide adenine dinucleotide (NAD) precursor to a pregnant female mammal, thereby causing improved glycemic control in the later born offspring. In certain embodiments, the method comprises administering an effective amount of a nicotinamide adenine dinucleotide (NAD) precursor to a lactating female mammal, wherein the offspring ingests milk from the lactating female mammal, thereby causing improved glycemic control in the offspring. In certain embodiments, the improved glycemic control results when the offspring is a baby. Thus, certain embodiments of the invention provide a method for improving glycemic control in a mammalian baby, comprising 1) administering an effective amount of a nicotinamide adenine dinucleotide (NAD) precursor to a pregnant female mammal, thereby causing improved glycemic control in the later born mammalian baby; and/or 2) administering an effective amount of a nicotinamide adenine dinucleotide (NAD) precursor to a lactating female mammal, wherein the mammalian baby ingests milk from the lactating female mammal, thereby causing improved glycemic control in the mammalian baby. In certain embodiments, the method comprises administering an effective amount of a nicotinamide adenine dinucleotide (NAD) precursor to a pregnant female mammal, thereby causing improved glycemic control in the later born mammalian baby. In certain embodiments, the method comprises administering an effective amount of a nicotinamide adenine dinucleotide (NAD) precursor to a lactating female mammal, wherein the mammalian baby ingests milk from the lactating female mammal, thereby causing improved glycemic control in the baby.

In certain embodiments, glycemic control is improved by at least about 1%, 2%, 3%, 4%, 5%, 6%, 7%, 8%, 9%, 10% or more (e.g., as compared to a control, such as to the glycemic control of an offspring from a mother not administered an NAD precursor). In certain embodiments, blood glucose levels from the offspring (e.g., baby) are within a normal range.

As used herein, the term "glycemic control" refers to the ability to maintain blood glucose levels within a normal range (i.e., not hypo- or hyper-glycemic). Glucose levels may be measured using techniques known within the art, for example, using an assay described in the Examples. In certain embodiments, glucose levels may be determined from a blood sample take from the offspring, such as a baby, (e.g., after fasting).

In certain embodiments, the health benefit is increased brain mass. Thus, certain embodiments of the invention provide a method for increasing brain mass in the offspring of a female mammal, comprising 1) administering an effective amount of a nicotinamide adenine dinucleotide (NAD) precursor to a pregnant female mammal, thereby causing increased brain mass in the later born offspring; and/or 2) administering an effective amount of a nicotinamide adenine dinucleotide (NAD) precursor to a lactating female mammal, wherein the offspring ingests milk from the lactating female mammal, thereby causing increased brain mass in the offspring. In certain embodiments, the method comprises administering an effective amount of a nicotinamide adenine dinucleotide (NAD) precursor to a pregnant female mammal, thereby causing increased brain mass in the later born offspring. In certain embodiments, the method comprises administering an effective amount of a nicotinamide adenine dinucleotide (NAD) precursor to a lactating female mammal, wherein the offspring ingests milk from the lactating female mammal, thereby causing increased brain mass in the offspring. In certain embodiments, the brain mass is increased by at least about 0.25%, 0.5%, 1%, 2%, 3%, 4%, 5% or more (e.g., as compared to a control, such as to the brain mass of offspring from a mother not administered an NAD precursor). In certain embodiments, the offspring's brain has more highly developed white matter. In certain embodiments, the offspring has improved cognitive and/or behavioral functions. In certain embodiments, the offspring is a male. In certain embodiments, the offspring is a female. Brain mass may be measured using techniques known in the art, for example, using brain scans. In certain embodiments, the increased brain mass occurs when the offspring is an adult. In certain embodiments, the increased brain mass occurs when the offspring is a baby. Thus, certain embodiments of the invention provide a method for increasing brain mass in a mammalian baby, comprising 1) administering an effective amount of a nicotinamide adenine dinucleotide (NAD) precursor to a pregnant female mammal, thereby causing increased brain mass in the later born mammalian baby; and/or 2) administering an effective amount of a nicotinamide adenine dinucleotide (NAD) precursor to a lactating female mammal, wherein the mammalian baby ingests milk from the lactating female mammal, thereby causing increased brain mass in the mammalian baby. In certain embodiments, the method comprises administering an effective amount of a nicotinamide adenine dinucleotide (NAD) precursor to a pregnant female mammal, thereby causing increased brain mass in the later born mammalian baby. In certain embodiments, the method comprises administering an effective amount of a nicotinamide adenine dinucleotide (NAD) precursor to a lactating female mammal, wherein the mammalian baby ingests milk from the lactating female mammal, thereby causing increased brain mass in the mammalian baby. In certain embodiments, the brain mass is increased by at least about 0.25%, 0.5%, 1%, 2%, 3%, 4%, 5% or more (e.g., as compared to a control, such as to the brain mass of a baby from a mother not administered an NAD precursor).

In certain embodiments, the baby's brain has more highly developed white matter. In certain embodiments, the baby has improved cognitive and/or behavioral functions. In certain embodiments, the baby is a male. In certain embodiments, the baby is a female.

In certain embodiments, the health benefit is increase physical activity. Thus, certain embodiments of the invention provide a method for increasing physical activity in the offspring of a female mammal, comprising 1) administering an effective amount of a nicotinamide adenine dinucleotide (NAD) precursor to a pregnant female mammal, thereby causing increased physical activity in the later born offspring; and/or 2) administering an effective amount of a nicotinamide adenine dinucleotide (NAD) precursor to a lactating female mammal, wherein the offspring ingests milk from the lactating female mammal, thereby causing increased physical activity in the offspring. In certain embodiments, the method comprises administering an effective amount of a nicotinamide adenine dinucleotide (NAD) precursor to a pregnant female mammal, thereby causing increased physical activity in the later born offspring. In certain embodiments, the method comprises administering an effective amount of a nicotinamide adenine dinucleotide (NAD) precursor to a lactating female mammal, wherein the offspring ingests milk from the lactating female mammal, thereby causing increased physical activity in the offspring. In certain embodiments, physical activity is increased by at least about 10%, 20%, 30%, 40%, 50%, 60%, 70%, 80%, 90%, 95% or more (e.g., as compared to a control, such as to the physical activity of an offspring from a mother not administered an NAD precursor). In certain embodiments, the increase in physical activity is experienced when the offspring is an adult. In certain embodiments, the increase in physical activity is experienced throughout the life of the offspring. In certain embodiments, the increase in physical activity is experienced when the offspring is a baby. Thus, certain embodiments of the invention provide a method for increasing physical activity in a mammalian baby, comprising 1) administering an effective amount of a nicotinamide adenine dinucleotide (NAD) precursor to a pregnant female mammal, thereby causing increased physical activity in the later born mammalian baby; and/or 2) administering an effective amount of a nicotinamide adenine dinucleotide (NAD) precursor to a lactating female mammal, wherein the mammalian baby ingests milk from the lactating female mammal, thereby causing increased physical activity in the mammalian baby. In certain embodiments, the method comprises administering an effective amount of a nicotinamide adenine dinucleotide (NAD) precursor to a pregnant female mammal, thereby causing increased physical activity in the later born mammalian baby. In certain embodiments, the method comprises administering an effective amount of a nicotinamide adenine dinucleotide (NAD) precursor to a lactating female mammal, wherein the mammalian baby ingests milk from the lactating female mammal, thereby causing increased physical activity in the mammalian baby. In certain embodiments, physical activity is increased by at least about 10%, 20%, 30%, 40%, 50%, 60%, 70%, 80%, 90%, 95% or more (e.g., as compared to a control, such as to the physical activity of a baby from a mother not administered an NAD precursor).

As used herein, the term "physical activity" refers to bodily movement. For example, physical activity could be assessed by measuring time spent moving versus time spent at rest. Other methods for measuring physical activity are known in the art, for example, using an assay described in the Examples.

In certain embodiments, the health benefit is improved development in the offspring. Thus, certain embodiments of the invention provide a method for improving development in the offspring of a female mammal, comprising 1) administering an effective amount of a nicotinamide adenine dinucleotide (NAD) precursor to a pregnant female mammal, thereby improving development in the later born offspring; and/or 2) administering an effective amount of a nicotinamide adenine dinucleotide (NAD) precursor to a lactating female mammal, wherein the offspring ingests milk from the lactating female mammal, thereby improving development in the offspring. In certain embodiments, the method comprises administering an effective amount of a nicotinamide adenine dinucleotide (NAD) precursor to a pregnant female mammal, thereby causing improved development in the later born offspring. In certain embodiments, the method comprises administering an effective amount of a nicotinamide adenine dinucleotide (NAD) precursor to a lactating female mammal, wherein the offspring ingests milk from the lactating female mammal, thereby causing improved development in the offspring (e.g., as compared to the development of offspring from a mother not administered an NAD precursor). In certain embodiments, the improved development is experienced when the offspring is a baby. In certain embodiments, the improved development is experienced when the offspring is an adult. In certain embodiments, the improved development is experienced throughout the life of the offspring. In certain embodiments, the offspring has advanced brain and/or neurocognitive development and/or physical function (e.g., as compared to the development of offspring from a mother not administered an NAD precursor).

As used herein, the term "development" may refer to physical development or function, as well as cognitive development or function. In certain embodiments, the development is physical development (e.g., development of gross and/or fine motor skills). In certain embodiments, the development is cognitive development (e.g., development of information processing, conceptual resources, perceptual skill, and/or language learning). Methods for measuring physical and cognitive development are known in the art, for example, using an assay described in the Examples.

In certain embodiments, the health benefit is improved physical abilities (e.g., coordination) in the offspring. Thus, certain embodiments of the invention provide a method for improving physical abilities in the offspring of a female mammal, comprising 1) administering an effective amount of a nicotinamide adenine dinucleotide (NAD) precursor to a pregnant female mammal, thereby improving physical abilities in the later born offspring; and/or 2) administering an effective amount of a nicotinamide adenine dinucleotide (NAD) precursor to a lactating female mammal, wherein the offspring ingests milk from the lactating female mammal, thereby improving physical abilities in the offspring. In certain embodiments, the method comprises administering an effective amount of a nicotinamide adenine dinucleotide (NAD) precursor to a pregnant female mammal, thereby causing improved physical abilities in the later born offspring. In certain embodiments, the method comprises administering an effective amount of a nicotinamide adenine dinucleotide (NAD) precursor to a lactating female mammal, wherein the offspring ingests milk from the lactating female mammal, thereby improving physical abilities in the offspring (e.g., as compared to the physical abilities of offspring from a mother not administered an NAD precursor). In certain embodiments, the improved physical abilities is experienced when the offspring is a baby. In certain embodiments, the improved physical abilities is experienced when the offspring is an adult. In certain embodiments, the improved physical abilities is experienced throughout the life of the offspring.

As used herein, the term "physical abilities" refers to the ability to perform a physical act. For example, physical abilities include those that influence, e.g., strength, endurance, flexibility, balance and coordination. Thus, in certain embodiments, the offspring may have improved strength, endurance, flexibility, balance and/or coordination. Methods for measuring improved physical abilities are known in the art, for example, as described in the Examples.

In certain embodiments, the health benefit is protection against age-induced weight gain. Thus, certain embodiments of the invention provide a method for protecting against age-induced weight gain in the offspring of a female mammal, comprising
  1) administering an effective amount of a nicotinamide adenine dinucleotide (NAD) precursor to a pregnant female mammal, thereby protecting against age-induced weight gain in the later born offspring; and/or
  2) administering an effective amount of a nicotinamide adenine dinucleotide (NAD) precursor to a lactating female mammal, wherein the offspring ingests milk from the lactating female mammal, thereby protecting against age-induced weight gain in the offspring. In certain embodiments, the method comprises administering an effective amount of a nicotinamide adenine dinucleotide (NAD) precursor to a pregnant female mammal, thereby protecting against age-induced weight gain in the later born offspring. In certain embodiments, the method comprises administering an effective amount of a nicotinamide adenine dinucleotide (NAD) precursor to a lactating female mammal, wherein the offspring ingests milk from the lactating female mammal, thereby protecting against age-induced weight gain in the offspring (e.g., as compared to the age-induced weight gain of offspring from a mother not administered an NAD precursor). In certain embodiments, age-induced weight gain is reduced by at least about 10%, 20%, 30%, 40%, 50%, 60%, 70%, 80%, 90%, 95% or more (e.g., as compared to a control, such as to the amount of weight gained during a specified time period during adulthood by a female mammal not administered an NAD precursor).

As used herein, the term "age-induced weight gain" refers to weight gained due to changes in the body composition during aging. Thus, age-induced weight gain would be evaluated, e.g., over a specified period of time during the adult stage of life. In certain embodiments, a mammal's weight at the beginning of adulthood could be compared to the mammal's weight later in life to determine the age-induced weight gain. Methods of evaluating age-induced weight gain are known in the art.

In certain embodiments, the health benefit is reduced anxiety. Thus, certain embodiments of the invention provide a method for reducing anxiety in the offspring of a female mammal, comprising
  1) administering an effective amount of a nicotinamide adenine dinucleotide (NAD) precursor to a pregnant female mammal, thereby causing reduced anxiety in the later born offspring; and/or
  2) administering an effective amount of a nicotinamide adenine dinucleotide (NAD) precursor to a lactating female mammal, wherein the offspring ingests milk from the lactating female mammal, thereby causing reduced anxiety in the offspring. In certain embodiments, the method comprises administering an effective amount of a nicotinamide adenine dinucleotide (NAD) precursor to a pregnant female mammal, thereby causing reduced anxiety in the later born offspring. In certain embodiments, the method comprises administering an effective amount of a nicotinamide adenine dinucleotide (NAD) precursor to a lactating female mammal, wherein the offspring ingests milk from the lactating female mammal, thereby causing reduced anxiety in the offspring. In certain embodiments, anxiety is reduced by at least about 10%, 20%, 30%, 40%, 50%, 60%, 70%, 80%, 90%, 95% or more (e.g., as compared to a control, such as to the anxiety of offspring from a mother not administered an NAD precursor). In certain embodiments, the reduced anxiety is experienced when the offspring is a baby. In certain embodiments, the reduced anxiety is experienced when the offspring is an adult. In certain embodiments, the reduced anxiety is experienced throughout the life of the offspring.

As used herein, the term "anxiety" is used to refer to various disorders that cause nervousness, fear, apprehension, and/or worrying. Thus, in certain embodiments, the offspring would be less nervous, have reduced fear, less apprehension and/or worry less.

Certain embodiments of the invention provide a method for increasing uncoupling protein 1 (UCP1) expression (e.g., mRNA levels or protein levels) in a cell in a mammal in need thereof, comprising contacting the cell with an effective amount of a nicotinamide adenine dinucleotide (NAD) precursor. In certain embodiments, the cell is contacted by administering the NAD precursor to the mammal (e.g., orally or topically).

Certain embodiments of the invention provide a method of increasing heat loss in a mammal, comprising administering an effective amount of a nicotinamide adenine dinucleotide (NAD) precursor to a mammal in need thereof. In certain embodiments, uncoupling protein 1 (UCP1) expression (e.g., mRNA levels or protein levels) is increased (e.g., by at least about 10%, 20%, 30%, 40%, 50%, 60%, 70%, 80%, 90%, 95% or more (e.g., as compared to a control, such as to the expression level in a mammal that was not administered an NAD precursor)).

The term "mammal" refers to any mammalian species such as a human, mouse, rat, dog, cat, hamster, guinea pig, rabbit, livestock (e.g., a cow, sheep, horse, pig, chicken, etc.), and the like. Accordingly, in certain embodiments, the mammal is a human, mouse, rat, dog, cat, hamster, guinea pig, rabbit or livestock. In certain embodiments, the mammal is a human. In certain embodiments, the mammal is pregnant. In certain embodiments, the mammal has given birth within the last year, or within the last 11, 10, 9, 8, 7, 6, 5, 4, 3, 2 or 1 month(s). In certain embodiments, the mammal is lactating.

In certain embodiments, the NAD precursor is administered to the female mammal once to three times daily.

In certain embodiments, the NAD precursor is administered to the female mammal prior to conception. In certain embodiments, the NAD precursor is administered to the female mammal starting, e.g., 1 day to 1 year prior to conception. In certain embodiments, the NAD precursor is administered to the female mammal starting, e.g., 1 day, 1 week, 1, 2, 3, 4, 5, 6, 7, 8, 9, 10 or 11 months prior to conception. In certain embodiments, the NAD precursor is administered to a pregnant female mammal. In certain embodiments, the NAD precursor is administered to a lactating female mammal. In certain embodiments, the NAD precursor is administered to a female mammal post-pregnancy. In certain embodiments, the NAD precursor is administered to a female mammal that has given birth within the last 3 years, 2 years, 1 year, or the last 11, 10, 9, 8, 7, 6, 5, 4, 3, 2 or 1 month(s).

In certain embodiments, the NAD precursor is administered orally, transmucosally (e.g., nasally), via inhalation or topically. In certain embodiments, the NAD precursor is administered orally. In certain embodiments, the NAD precursor is administered via an injection. In certain embodiments, the NAD precursor is administered transdermally. In certain embodiments, the NAD precursor is formulated as a pill, a powder, a nasal spray or solution, or as an ointment or cream. In certain embodiments, the NAD precursor is in a lipophilic formulation.

In certain embodiments, the methods of the invention may further comprise the administration of a second biologically active agent. In certain embodiments, the second therapeutic agent is useful for modulating the absorption and/or distribution of the NAD precursor (e.g., improving the NAD precursor bioavailability). The second biologically active agent may be administered either simultaneously or sequentially with the NAD precursor. In certain embodiments, the second biologically active agent is administered simultaneously with the NAD precursor. In certain embodiments, a pharmaceutical composition comprising the NAD precursor and the second biologically active agent is administered. In certain embodiments, the NAD precursor and the second biologically active agent are administered sequentially. In certain embodiments, the NAD precursor is administered first and the second biologically active agent is administered second. In certain embodiments, the second biologically active agent is administered first and NAD precursor is administered second.

Certain embodiments of the invention provide a NAD precursor for use in medical therapy.

Certain embodiments of the invention provide a NAD precursor for reducing pregnancy associated weight gain and/or to promote post-pregnancy weight loss in a female mammal (e.g., a human).

Certain embodiments of the invention provide the use of a NAD precursor to prepare a medicament for reducing pregnancy associated weight gain and/or to promote post-pregnancy weight loss in a female mammal (e.g., a human) in need thereof.

Certain embodiments of the invention provide a NAD precursor for increasing milk production in a lactating mammal (e.g., a human).

Certain embodiments of the invention provide a NAD precursor for increasing milk quality a lactating mammal (e.g., a human).

Certain embodiments of the invention provide the use of a NAD precursor to prepare a medicament for increasing milk production in a lactating mammal (e.g., a human) in need thereof.

Certain embodiments of the invention provide a NAD precursor for improving metabolism in a mammal's baby (e.g., a human).

Certain embodiments of the invention provide the use of a NAD precursor to prepare a medicament for improving metabolism in a mammal's baby (e.g., a human) in need thereof.

Certain embodiments of the invention provide a NAD precursor for increasing glycemic control in a mammal's baby (e.g., a human).

Certain embodiments of the invention provide the use of a NAD precursor to prepare a medicament for increasing glycemic control in a mammal's baby.

Certain embodiments of the invention provide a NAD precursor for increasing brain mass in a mammal's baby (e.g., a human).

Certain embodiments of the invention provide the use of a NAD precursor to prepare a medicament for increasing brain mass in a mammal's baby.

Certain embodiments of the invention provide a NAD precursor for increasing physical activity in a mammal's baby (e.g., a human).

Certain embodiments of the invention provide the use of a NAD precursor to prepare a medicament for increasing physical activity in a mammal's baby.

Certain embodiments of the invention provide a composition (e.g., a pharmaceutical composition) for use in a method of the invention, comprising a NAD precursor, and an acceptable carrier (e.g., a pharmaceutically acceptable carrier).

Certain embodiments of the invention provide a composition (e.g., a pharmaceutical composition) for reducing pregnancy associated weight gain, for promoting post-pregnancy weight loss, for increasing milk production, for improving metabolism in the mammal's baby, for increasing glycemic control in the mammal's baby, for increasing brain mass in the mammal's baby and/or for increasing the physical activity of the mammal's baby, comprising a NAD precursor, and an acceptable carrier (e.g., a pharmaceutically acceptable carrier).

Certain embodiments of the invention provide a kit comprising a NAD precursor and instructions for administering the NAD precursor to a female mammal for reducing pregnancy associated weight gain, for promoting post-pregnancy weight loss, for increasing milk production, for improving metabolism in the mammal's baby, for increasing glycemic control in the mammal's baby, for increasing brain mass in the mammal's baby and/or for increasing the physical activity of the mammal's baby.

Certain embodiments of the invention provide a kit comprising 1) a composition (e.g., a pharmaceutical composition) comprising a NAD precursor and a carrier (e.g., a pharmaceutically acceptable carrier), wherein the composition is formulated for oral administration; and 2) instructions for orally administering the NAD precursor to a female mammal for reducing pregnancy associated weight gain, for promoting post-pregnancy weight loss, for increasing milk production, for improving metabolism in the mammal's baby, for increasing glycemic control in the mammal's baby, for increasing brain mass in the mammal's baby and/or for increasing the physical activity of the mammal's baby.

Thus, certain embodiments of the invention provide a NAD precursor, use or kit as described herein for imparting a health benefit to a female mammal in need thereof In certain embodiments, the NAD precursor, use or kit described herein is for administration to the female mammal pre-pregnancy, during pregnancy and/or post-pregnancy.

Certain embodiments of the invention provide a NAD precursor, use or kit as described herein for imparting a health benefit to the offspring of the female mammal. In certain embodiments, the NAD precursor, use or kit described herein is for administration to the female mammal while pregnant, whereby the health benefit is imparted to the later born offspring. In certain embodiments, the NAD precursor, use or kit described herein is for administration to the female mammal while lactating, wherein the offspring ingests milk from the lactating female mammal, thereby imparting the health benefit to the offspring.

NAD Precursors

As used herein, the term "NAD precursor" refers to molecules that can be converted/synthesized in vivo into NAD. NAD precursors are known in the art and include, for example, NR and derivatives and analogs thereof (e.g., nicotinoyl ribosides), as well as molecules that can be converted/synthesized in vivo into NR. NR is a natural product, is currently produced under GMP, has achieved FDA new dietary ingredient status, and is generally regarded as safe (Bieganowski & Brenner, Cell (2004), 117(4), 495-502; Trammell, et al., Journal of Nutrition (2016), 146(5), 957-963). Additionally, certain NAD precursors are discussed in WO 2006/116322, WO 2015014722, WO 2015186114, WO 2015186068, WO 2016014927, WO 2016/149277, WO 2016049236, WO 2015066382, U.S. Pat. No. 9,408,834, and Kulikova et al., Journal of Biological Chemistry (2015), 290(45), 27124-27137, which are incorporated by reference herein.

In certain embodiments, the NAD precursor is a compound of formula (I):

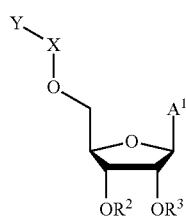

(I)

or a salt thereof (e.g., a pharmaceutically acceptable salt), wherein:

$A^1$ is

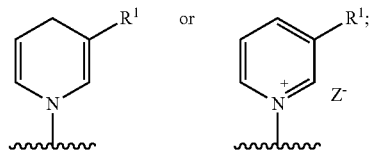

$R^1$ is —COOH, —C(=O)NH$_2$ or —C(=O)OR$^a$;
$R^2$ is H or (C$_1$-C$_3$)alkanoyl;
$R^3$ is H or (C$_1$-C$_3$)alkanoyl;
i) X is absent, —P(=O)(OW)(O—), or —P(=O)(OW)—O—P(=O)(OW)(O—); and
Y is W, or

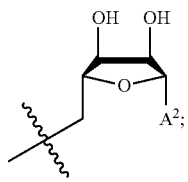

or
ii) X is absent; and Y is (C$_1$-C$_{10}$)alkanoyl;
$R^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$) alkoxy, (C$_1$-C$_3$)alkoxycarbonyl, aryl, and (C$_1$-C$_3$)alkanoyloxy;

each W is independently selected from the group consisting of H and pharmaceutically acceptable cations;

$A^2$ is

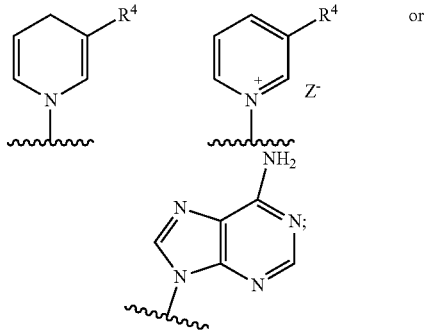

Z is a pharmaceutically acceptable anion;
$R^4$ is —COOH, —C(=O)NH$_2$, or —C(=O)OR$^b$;
$R^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$) alkoxy, (C$_1$-C$_3$)alkoxycarbonyl, aryl, and (C$_1$-C$_3$)alkanoyloxy;.

In certain embodiments, $R^1$ is —COOH or —C(=O)OR$^a$;
In certain embodiments, $R^1$ is —COOH.
In certain embodiments, $R^1$ is —C(=O)NH$_2$.
In certain embodiments, $R^1$ is not —C(=O)NH$_2$.
In certain embodiments, $R^1$ is —C(=O)OR$^a$.
In certain embodiments, $R^2$ is H.
In certain embodiments, $R^2$ is (C$_1$-C$_3$)alkanoyl.
In certain embodiments, $R^2$ is acyl.
In certain embodiments, $R^3$ is (C$_1$-C$_3$)alkanoyl.
In certain embodiments, $R^3$ is acyl.
In certain embodiments, X is absent, —P(=O)(O)(O—), or —P(=O)(OW)—O—P(=O)(OW)(O—); and
Y is W or

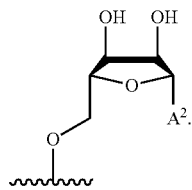

In certain embodiments, Y is

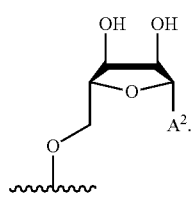

In certain embodiments, X is absent.

In certain embodiments, X is —P(=O)(OW)(O—), or —P(=O)(OW)—O—P(=O)(OW)(O—).

In certain embodiments, X is absent and Y is $(C_1\text{-}C_{10})$alkanoyl.

In certain embodiments, Y is acyl.

In certain embodiments, X is not absent and Y is not $(C_1\text{-}C_{10})$alkanoyl.

In certain embodiments, $R^a$ is $(C_1\text{-}C_{10})$alkyl.

In certain embodiments, each W is H.

In certain embodiments, each W is independently selected from the group consisting pharmaceutically acceptable cations.

In certain embodiments, each W is independently selected from sodium and potassium.

In certain embodiments, $A^2$ is

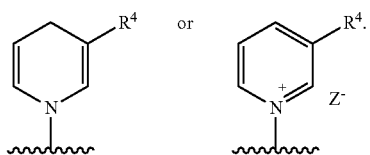

In certain embodiments, $A^2$ is

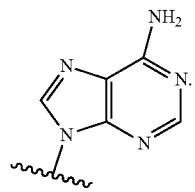 [SMILES: *n1cnc2c(N)ncnc21]

In certain embodiments, Z is chloride.

In one embodiment, the NAD precursor is a compound of formula (I):

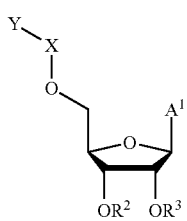

or a salt thereof (e.g., a pharmaceutically acceptable salt), wherein:

$A^1$ is

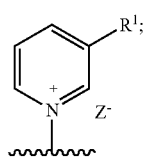

$R^1$ is —COOH, —C(=O)NH$_2$ or —C(=O)OR$^a$;
$R^2$ is $(C_1\text{-}C_3)$alkanoyl;
$R^3$ is $(C_1\text{-}C_3)$alkanoyl;
X is absent; and Y is $(C_1\text{-}C_{10})$alkanoyl;
$R^a$ is $(C_1\text{-}C_{10})$alkyl, $(C_2\text{-}C_{10})$alkenyl, or aryl, wherein each $(C_1\text{-}C_{10})$alkyl, $(C_2\text{-}C_{10})$alkenyl and aryl is optionally substitutes with one or more groups independently selected from the group consisting of halo, hydroxyl, cyano, $(C_1\text{-}C_3)$alkoxy, $(C_1\text{-}C_3)$alkoxycarbonyl, aryl, and $(C_1\text{-}C_3)$alkanoyloxy; and
Z is a pharmaceutically acceptable anion.

In one embodiment, the NAD precursor is a compound of formula (I):

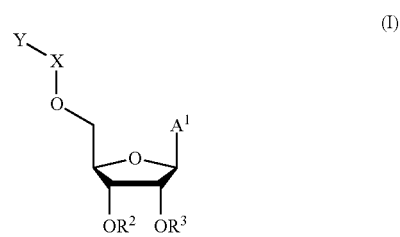

or a salt thereof (e.g., a pharmaceutically acceptable salt), wherein:

$A^1$ is

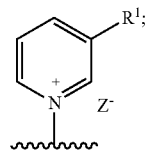

$R^1$ is —C(=O)OR$^a$;
$R^2$ is H or $(C_1\text{-}C_3)$alkanoyl;
$R^3$ is H or $(C_1\text{-}C_3)$alkanoyl;
X is absent;
Y is W or $(C_1\text{-}C_{10})$alkanoyl;
$R^a$ is $(C_1\text{-}C_{10})$alkyl, $(C_2\text{-}C_{10})$alkenyl, or aryl, wherein each $(C_1\text{-}C_{10})$alkyl, $(C_2\text{-}C_{10})$alkenyl and aryl is optionally substitutes with one or more groups independently selected from the group consisting of halo, hydroxyl, cyano, $(C_1\text{-}C_3)$alkoxy, $(C_1\text{-}C_3)$alkoxycarbonyl, aryl, and $(C_1\text{-}C_3)$alkanoyloxy;
each W is independently selected from the group consisting of H and pharmaceutically acceptable cations; and
Z is a pharmaceutically acceptable anion.

In certain embodiments, the compound of formula (I) is selected from the group consisting of:

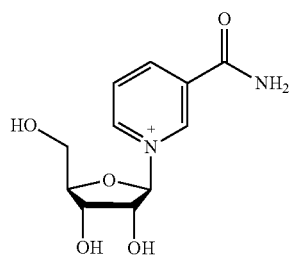

Nicotinamide riboside (NR)

-continued
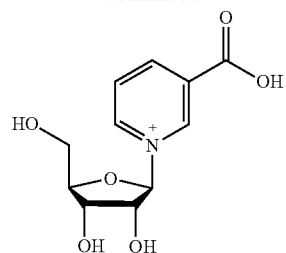
Nicotinic acid riboside (NAR)
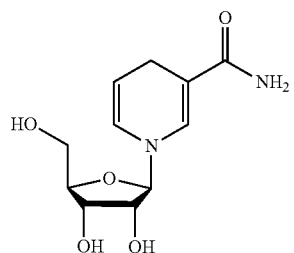
1,4-dihydronicotinamide riboside (NRH)
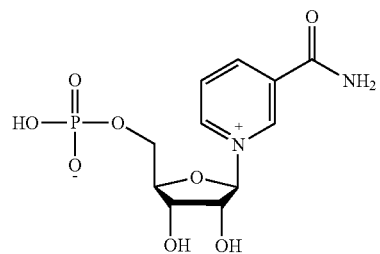
Nicotinamide mononucleotide (NMN)
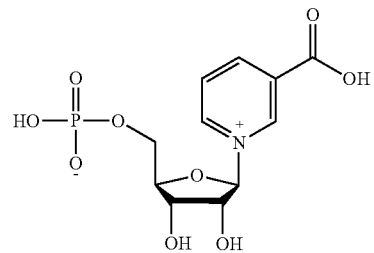
Nicotinic acid mononucleotide (NAMN)
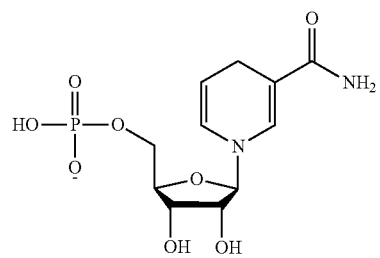
NMNH
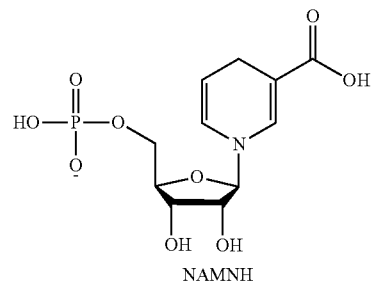
NAMNH
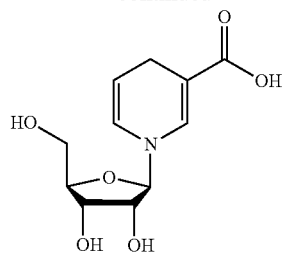
1,4-dihydronicotinic acid riboside (NARH)
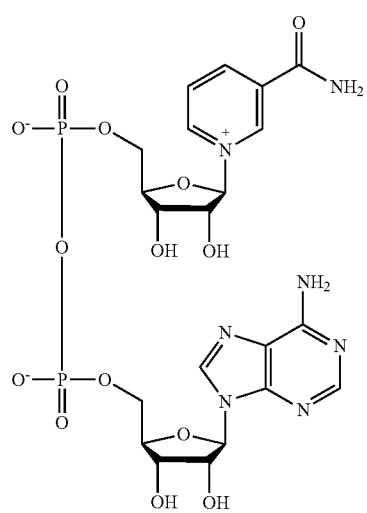
Nicotinamide Adenine Dinucleotide
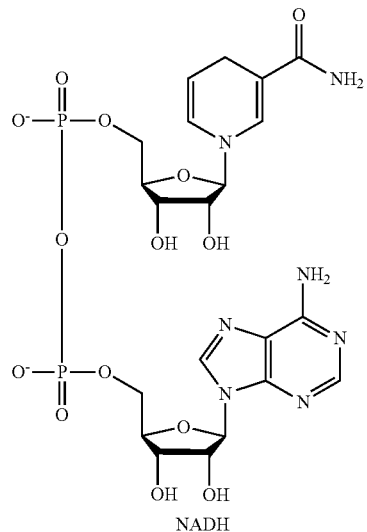
NADH

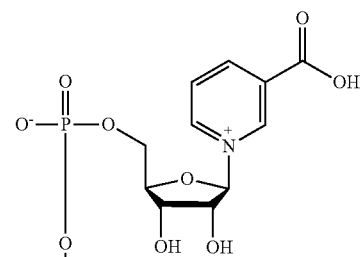
NAAD
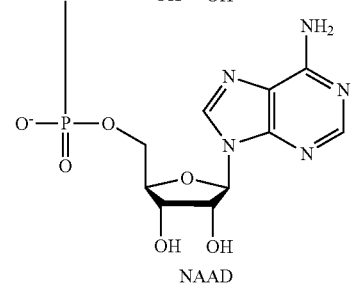
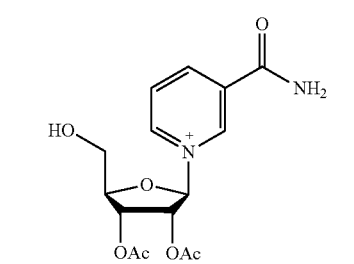
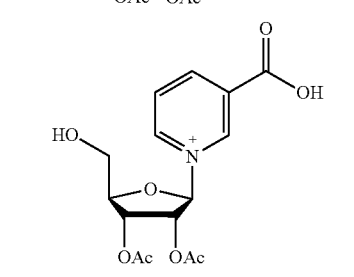
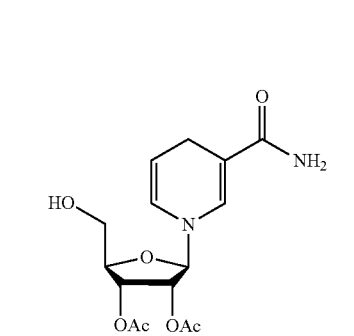
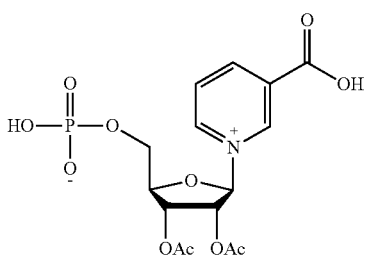
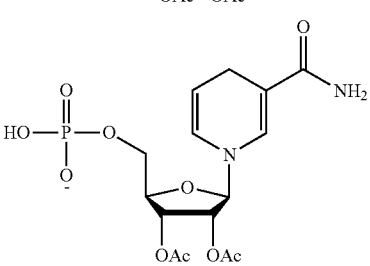
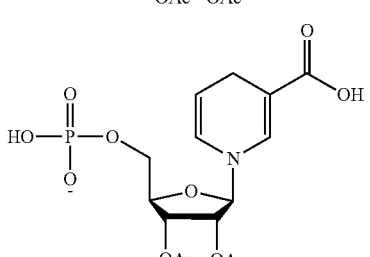
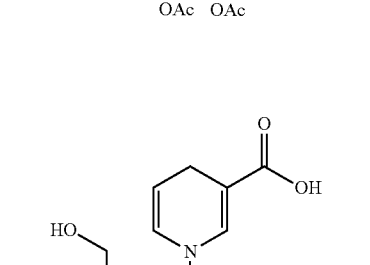
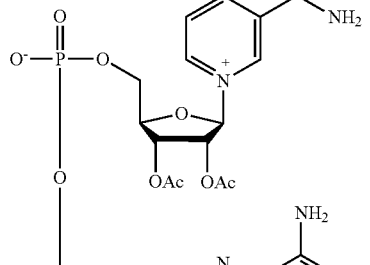

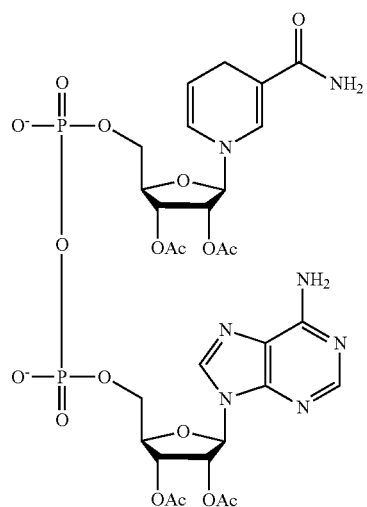

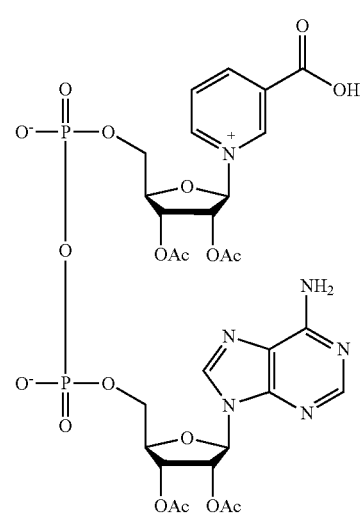

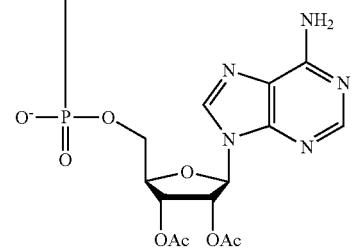

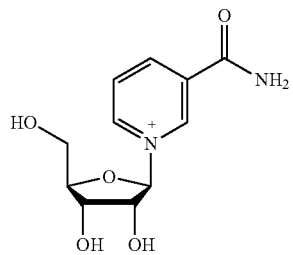

and salts thereof (e.g., pharmaceutically acceptable salts thereof).

In certain embodiments, the NAD precursor is NR:

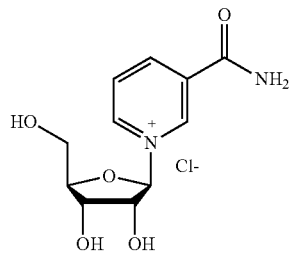

or a salt thereof (e.g., a pharmaceutically acceptable salt thereof).

In certain embodiments, the NAD precursor is NR chloride:

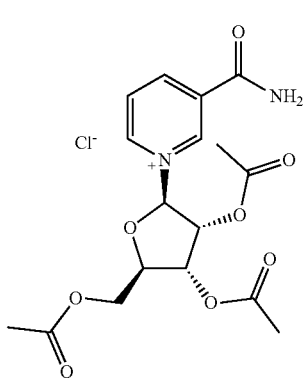

or a salt thereof (e.g., a pharmaceutically acceptable salt thereof).

In certain embodiments, the NAD precursor is not NAMNH. In certain embodiments, the NAD precursor is not NARH.

In certain embodiments, the NAD precursor is NAMNH. In certain embodiments, the NAD precursor is NARH.

The following definitions are used, unless otherwise described: halo is fluoro, chloro, bromo, or iodo. Alkyl, alkoxy, and alkenyl etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic.

Specific values listed below for radicals, substituents, and ranges, are for illustration only; they do not exclude other defined values or other values within defined ranges for the radicals and substituents.

Specifically, $(C_1-C_{10})$alkyl can be methyl, ethyl, propyl, isopropyl, butyl, iso-butyl, sec-butyl, pentyl, 3-pentyl, hexyl, heptyl, octyl, nonyl, or decyl; $(C_1-C_3)$alkoxy can be methoxy, ethoxy, or propoxy; $(C_2-C_{10})$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 5-hexenyl; 1-heptenyl, 1-octenyl, 1-nonenyl, or 1-decenyl; $(C_1-C_3)$ alkoxycarbonyl can be methoxycarbonyl, ethoxycarbonyl, or propoxycarbonyl, $(C_1-C_3)$alkanoyloxy can be formyloxy, acetoxy, or propanoyloxy; and aryl can be phenyl, indenyl, or naphthyl.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

It is understood that compounds of formula (I) that include both a positively charged nitrogen (e.g., a pyridinium nitrogen atom or quaternary nitrogen atom) and a carboxylic acid group may exist as a single molecule that possesses both a positive charge and a negative charge (e.g. a zwitterion). Accordingly, as used herein, the term "pharmaceutically acceptable salt" includes such zwitterions. For example, the compound 100 below represents a pharmaceutically acceptable salt of the compound 101.

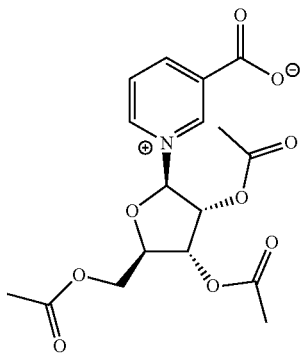

100

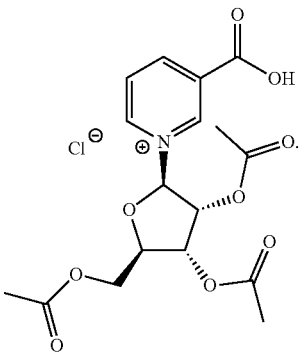

101

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically acceptable cations are well known in the art and include, sodium, potassium, magnesium and calcium.

Pharmaceutically acceptable anions are well known in the art and include, chloride, bromide, iodide, tosylate, methanesulfonate, acetate, citrate, malonate, tartarate, succinate, benzoate, ascorbate, α-ketoglutarate, and α-glycerophosphate.

Administration

A compound described herein for use in the invention can be formulated as a composition (e.g., a pharmaceutical composition) and administered to a mammalian host, such as a woman intending to become pregnant, a pregnant woman or a lactating mother, in a variety of forms adapted to the chosen route of administration, i.e., orally or parenterally, by intravenous, intramuscular, topical (e.g., transdermal, transmucosal), inhalation or subcutaneous routes.

Thus, the present compounds may be systemically administered, e.g., orally (e.g., added to drinking water), in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound may be combined with one or more excipients and used in the form of ingestible tablets, buccal tablets, troches, capsules, elixirs, suspensions, syrups, wafers, and the like. Such compositions and preparations should contain at least 0.1% of the compound. The percentage of the compositions and preparations may, of course, be varied and may conveniently be between about 2 to about 60% of the weight of a given unit dosage form. The amount of compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compound may be incorporated into sustained-release preparations and devices.

The compound may also be administered intravenously or intraperitoneally by infusion or injection. Solutions of the compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compounds may be conveniently formulated in unit dosage form. In one embodiment, the invention provides a composition comprising a compound formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

A NAD precursor can also be administered in combination with other therapeutic or biologically active agents, for example, other agents that are useful for modulating the absorption and/or distribution of the NAD precursor (e.g., improving the NAD precursor bioavailability, such as oral, nasal or topical bioavailability). Accordingly, in one embodiment the invention also provides a composition comprising an NAD precursor, at least one other therapeutic or biologically active agent, and a pharmaceutically acceptable diluent or carrier. The invention also provides a kit comprising a NAD precursor, at least one other therapeutic or biologically active agent, packaging material, and instructions for administering the NAD precursor and the other therapeutic/biologically active agent or agents to a female mammal to improve maternal, neonatal and/or child health.

The invention will now be illustrated by the following non-limiting Examples.

Example 1

Mice are a widely used model of human metabolism because they are capable of recapitulating many aspects of human health. Specifically, female mice gain substantial body fat in the course of pregnancy and, despite best animal husbandry practices, the fasting glucose levels of weaned pups can be slightly to significantly hypoglycemic. Therefore, mice were used in a series of in vivo experiments to evaluate whether maternally supplemented NR has the ability to improve maternal and/or neonatal health and development. Specifically, it was asked whether addition of NR chloride (3 g/kg of chow) to the diet of female mice would alter their health during and after pregnancy and whether this administration would produce any beneficial effects on the pups.

Methods

Female C57BL/6N mice were raised in 12 hour light:dark cycles on Teklad 2920X chow (NC). For 12 weeks prior to mating with a single C57BL/6N male, females were on either NC (n=4) or NC+NR (n=4). Females were maintained on the same diet through gestation and weaning, which was at 21 days after birth.

Results

As described herein, the provision of nicotinamide riboside (NR) in the diet of female mice resulted in 1) a near total elimination of weight gain over the gestational and post-gestational interval; 2) a significant increase in the amount of milk produced by lactating females; 3) leaner body mass of neonates at the time of weaning; 4) larger brain mass of neonates at the time of weaning; 5) greater physical activity of fasted neonates; and 6) correction of neonatal glycemic control from a slightly low level to an ideal level.

Specifically, as shown in FIG. 1, females on NC gained nearly 15% of their body weight from the day of mating to the day of weaning, whereas females supplemented with NR were protected from this weight gain. Further, it was determined that at the time of weaning, NR-supplemented mothers tended to have lower body fat.

Figure 2:
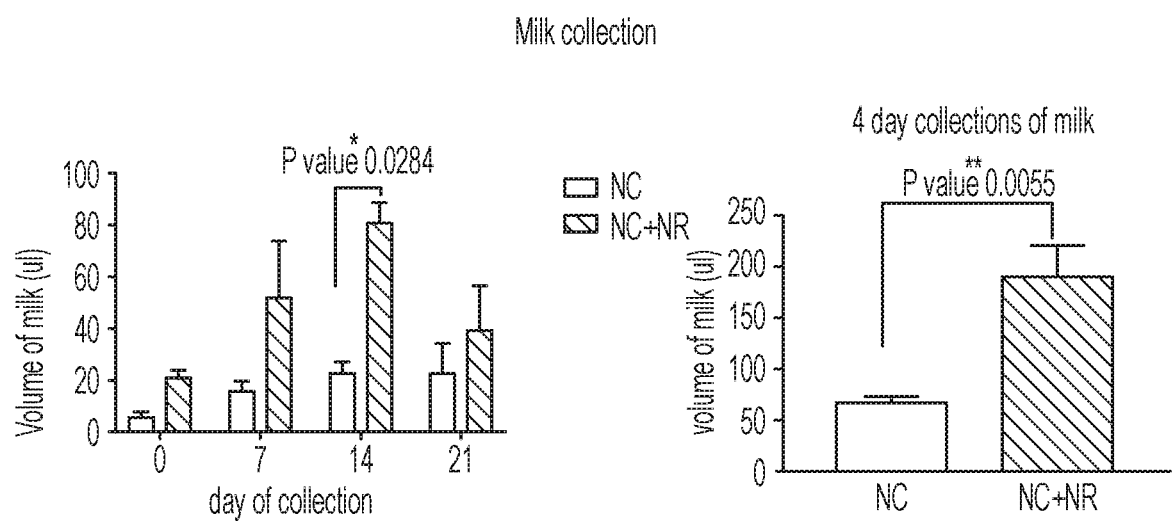
FIG. 2. Volume of milk collected from lactating female mice fed NC or NC+NR.

FIG. 2 demonstrates that females supplemented with NR had a 2-3x increase in milk production. To determine the production of milk, we separated mothers were separated from pups for several hours and provided an injection of oxytocin on days 0, 7, 14 and 21 after partum. Milk was carefully collected by pipetting and the collected volume per mother was plotted. The galactogogue activity of NR was striking and entirely unexpected.

Figure 3:
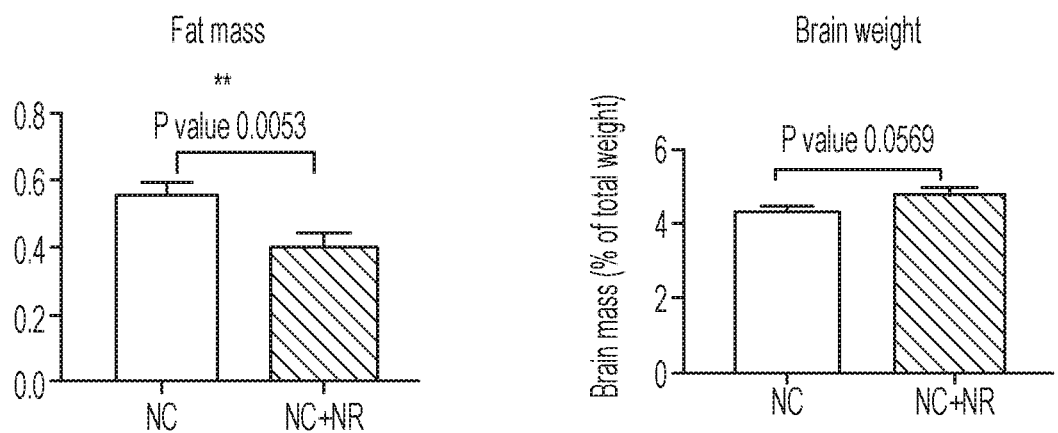
FIG. 3. Fat mass (left panel) and brain mass (right panel) from mice raised by mothers fed NC or NC+NR.

FIG. 3 shows that mice raised by NR-supplemented mothers are leaner and tend toward larger brains at weaning. The improved body composition of mice from NR-supplemented mothers was entirely unexpected.

Figure 4:
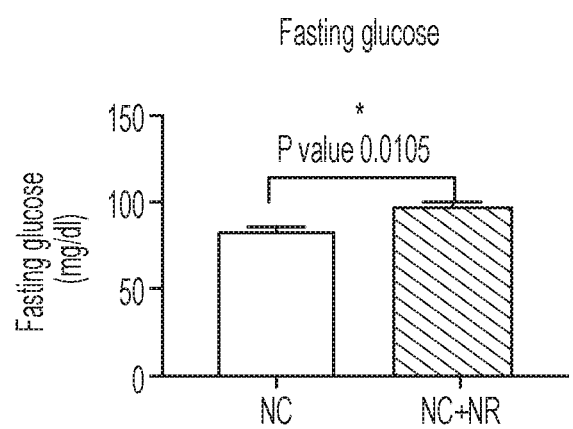
FIG. 4. Fasting glucose of mice raised by mothers fed NC or NC+NR.

FIG. 4 shows that mice raised by NR-supplemented mothers are better at maintaining glucose after an overnight fast. The mild hypoglycemia of mice on standard chow was not expected and the improvement in glycemic control by virtue of supplementing mothers was unexpected.

Example 2

Figure 5:
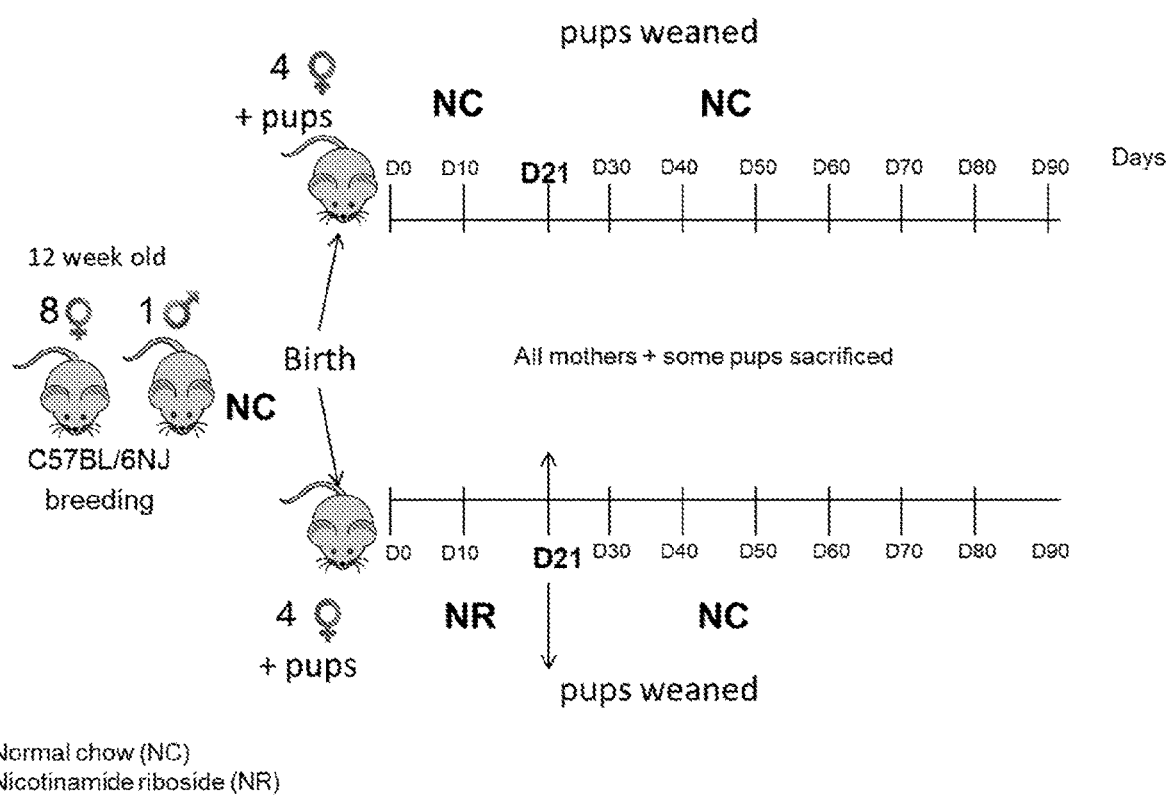
FIG. 5. Experimental design.
Figure 6A:
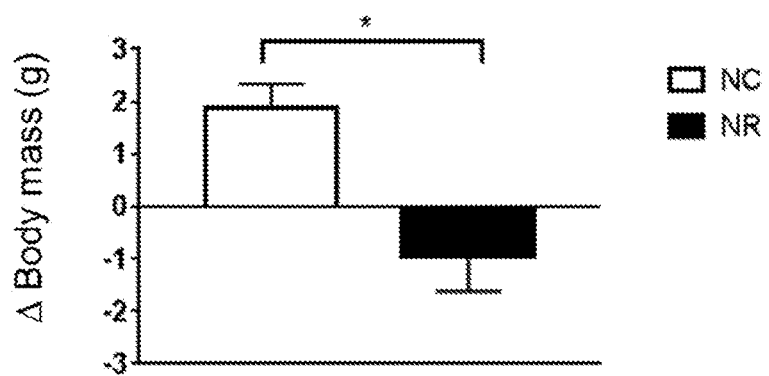
FIGS. 6A-D. NR-supplemented mouse mothers lose weight during the 21 day lactation period without diminished food consumption (day 7-21). Delta body mass refers to day 21 post-partum maternal weight minus day 0 post-partum weight (FIG. 6A). Food consumption was day 7-21 (FIG. 6B). NR-supplemented mothers tend to lose fat (FIG. 6C) and maintain lean mass (FIG. 6D). Body composition refers to day 21 post-partum maternal fat and lean mass minus day 0 post-partum maternal fat and lean mass.
Figure 6B:
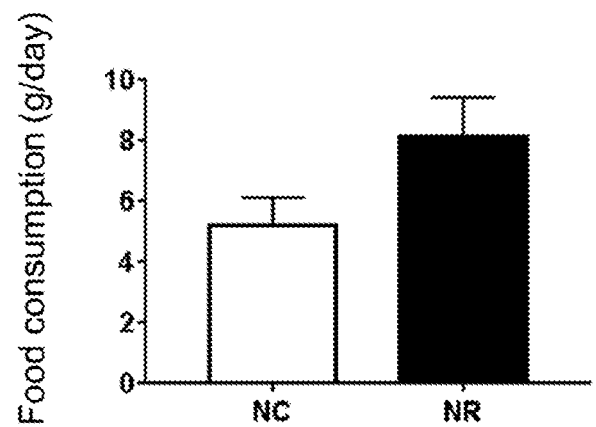
Figure 6C:
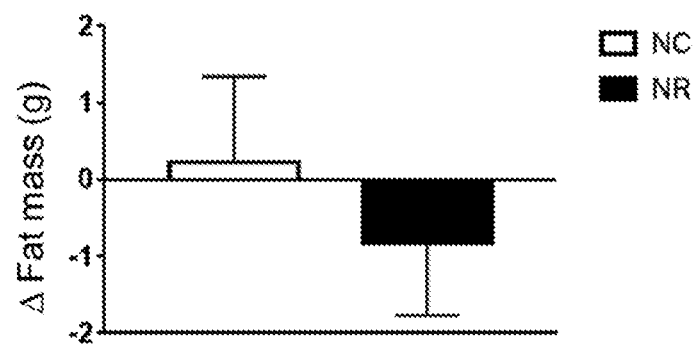
Figure 6D:
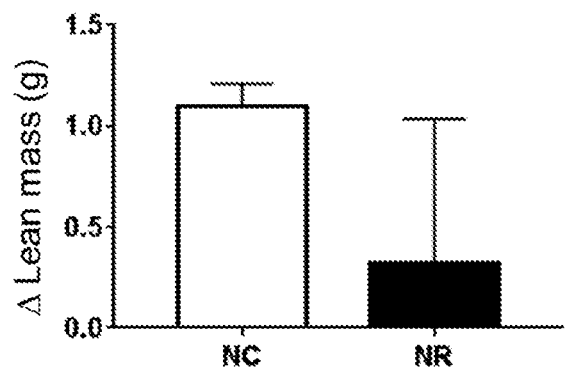

A series of in vivo murine experiments were performed to evaluate whether maternally supplemented NR has the ability to improve maternal and neonatal health and development. Note that in these and subsequent experiments and as shown in FIG. 5, NR was only provided to mouse mothers after they had given birth. As shown in FIGS. 6A-D, mothers supplemented with NR ate as least as much as non-supplemented mothers but lost significant weight, specifically in fat mass, while they maintained their lean mass. These data confirm that NR supplementation increases post-gestational weight loss and that NR supplementation can begin post-partum in order to have this effect.

Example 3

Nicotinamide riboside increases the quantity and quality of milk by stimulating lactation and stimulating the production of brain derived neurotrophic factor (BDNF).

Figure 7:
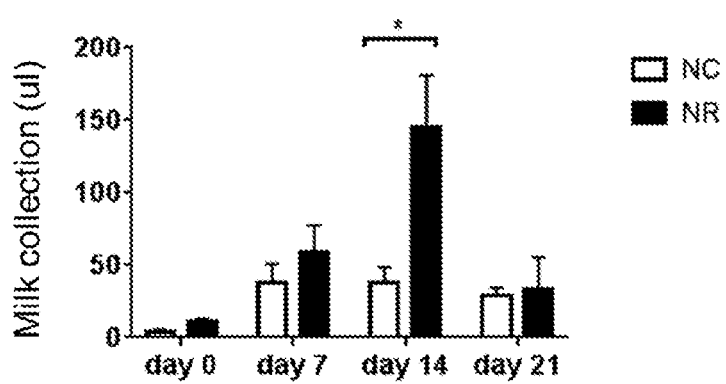
FIG. 7. NR-supplemented mothers produced more milk.
Figure 8A:
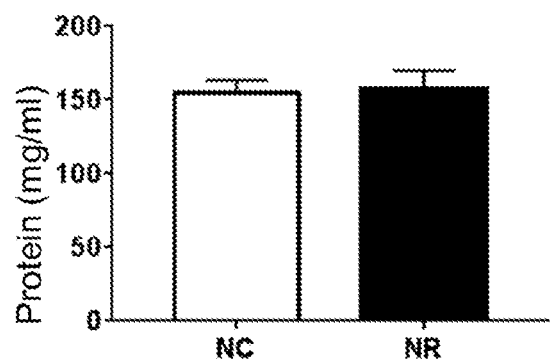
FIGS. 8A-C. Milk from NR-supplemented mothers had normal macronutrient density. Oxytocin-induced milk collection at indicated days. Protein (FIG. 8A), carbohydrate (FIG. 8B) and lipid concentration (FIG. 8C) was not changed.
Figure 8B:
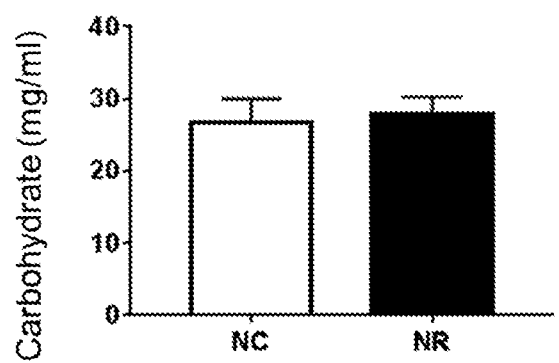
Figure 8C:
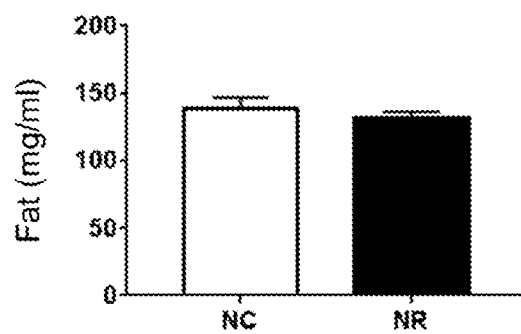
Figure 9A:
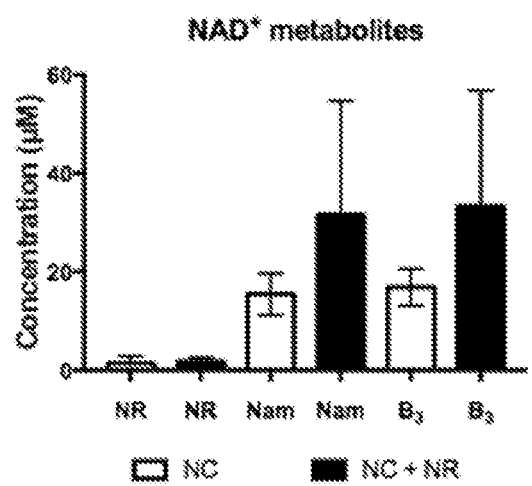
FIGS. 9A-B. Orally administered NR is not directly transmitted via milk. The concentration of nicotinamide and NR was slightly increased when mother was NR-supplemented. However, when mother was given oral NR with heavy atoms in the nicotinamide and ribose moieties of NR, mass spec analysis indicates that some of the milk nicotinamide is labeled but not of the milk NR is labeled. This indicates that oral NR to the mother has some somatic target in the mother that increases her milk production but that maternally ingested NR is not directly transmitted to the offspring.
Figure 9B:
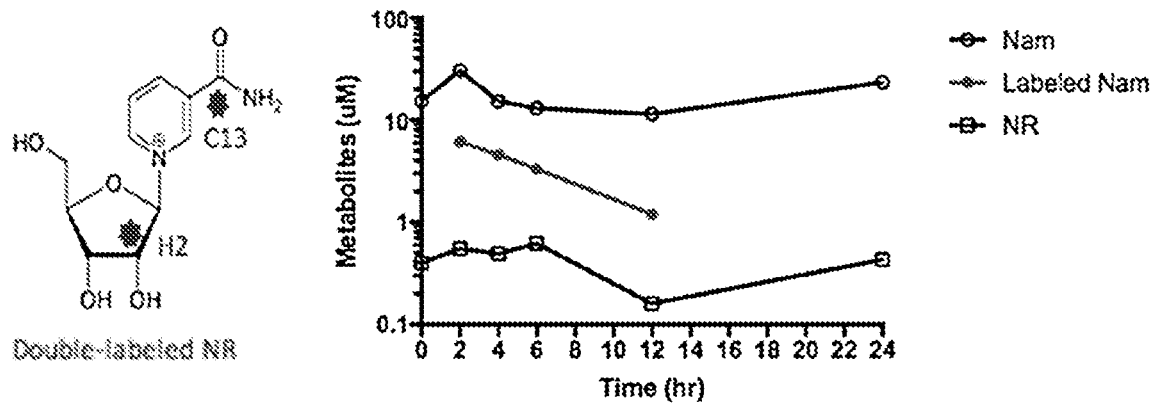

A series of in vivo murine experiments were performed to evaluate the effects of nicotinamide riboside on milk production. As shown in FIG. 7, the large increase in milk production was reproduced by virtue of supplementing post-gestational mothers. As shown in FIGS. 8A-C, the concentration of protein, carbohydrate and fat in the milk of NR-supplemented mothers was normal. Because there is approximately 2-fold more milk produced by NR-supplemented mothers, NR-supplemented mothers transmit more calories to their offspring, which thereby assists maternal weight loss and neonatal development. In FIG. 9A, the concentration of NAD precursor vitamins in the milk from control mothers and NR-supplemented mothers was determined. It was discovered that the milk from NR-supplemented mothers has moderately higher nicotinamide (Nam) and NR by concentration than the milk from non-supplemented mothers. Coupled with the larger milk volume, NR-supplemented mothers transmit significantly more NAD precursor vitamins (total B3) than the non-supplemented mothers. As shown in FIG. 9B, it was investigated whether oral NR is directly transmitted to offspring in milk or whether it has maternal targets. Oral NR was labeled with heavy atoms in the nicotinamide and ribose moieties of NR and this was provided to lactating mothers by gavage. The mothers released only single labeled nicotinamide and no double-labeled NR into their milk. These data indicate that the targets of maternal NR are in stimulation of her metabolic processes and are not simply confined to passing through oral NR to milk NR.

Figure 10:
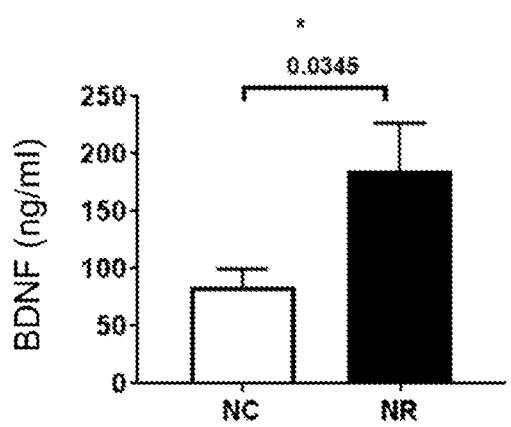
FIG. 10. NR supplemented mothers produce milk with higher brain-derived neurotrophic factor. Milk from NC and NR mothers was tested. NR-supplemented mothers have 2-fold higher levels of BDNF in the milk, suggesting a powerful mechanism by which NR supplementation supports neonatal development and health.

Based on the advanced brain and neurobehavioral development that was observed, it was investigated whether NR-supplemented mothers produced more BDNF in their milk. Surprisingly, as shown in FIG. 10, there was a 2-fold higher concentration of BDNF in the milk of NR-supplemented mothers than in non-supplemented mothers. Given that NR-supplemented mothers also produced more milk, NR-supplementation results in a large increase of maternally produced BDNF to aid neonatal development.

Example 4

Lactation and maternal nicotinamide riboside mobilize NAD precursors from the liver to the mammary gland.

Figure 11A:
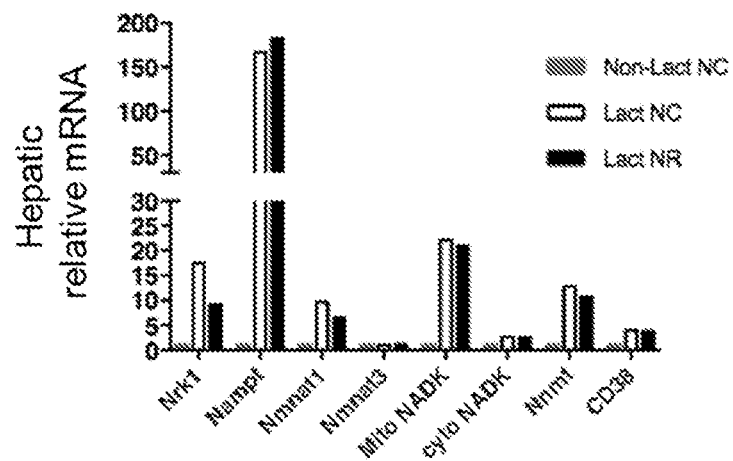
FIGS. 11A-D. Lactation but not NR boosts hepatic NAD biosynthesis but not accumulation of NAD metabolites in the liver, suggesting that lactation drives the liver to mobilize NAD metabolites elsewhere. Lactation boosts NAD biosynthetic genes (FIG. 11A) and NAD levels (FIG. 11B) in the liver. NR does not superinduce in the liver.
Figure 11B:
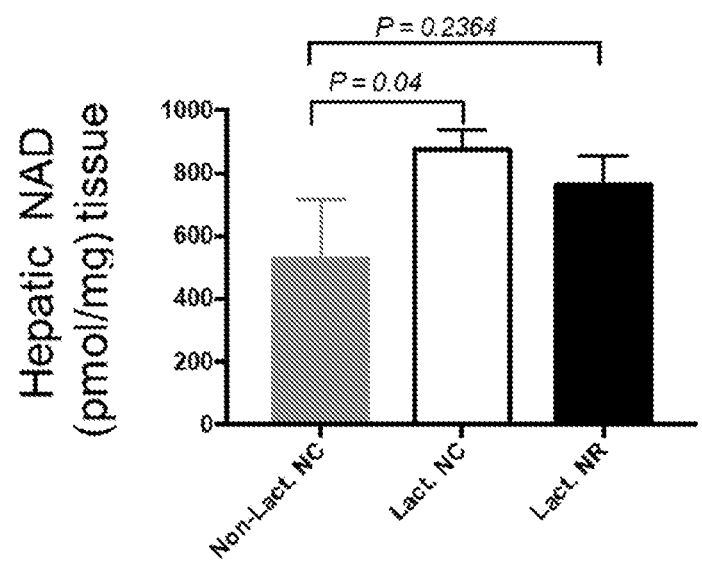
Figure 11C:
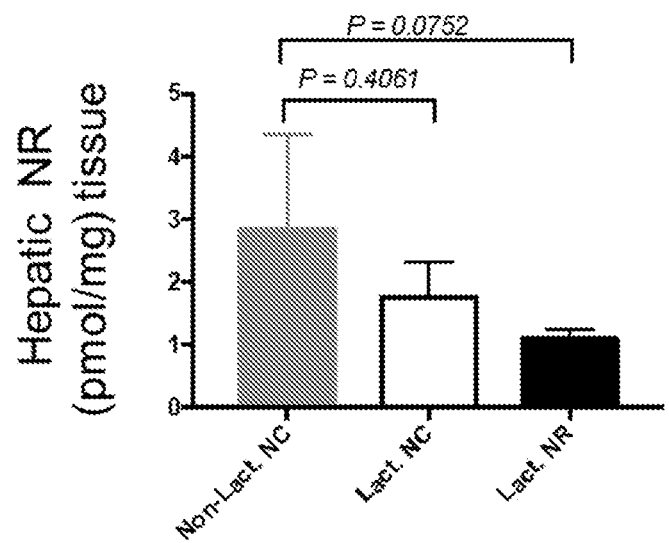
Figure 11D:
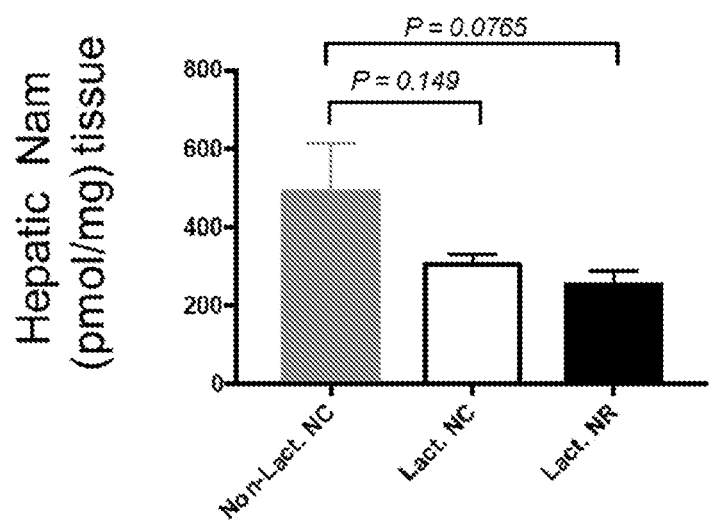

As shown in FIG. 11A, the RNA expression of NAD biosynthetic genes in the liver of female virgin mice versus the livers of lactating mice without or with NR supplementation was examined. Lactation greatly increased expression of NAD biosynthetic genes, especially NAMPT, NRK1, NMNAT1 and NADK. Lactation also increased expression of CD38, suggesting that the lactating liver is making more NAD from multiple precursors and then breaking it down for circulation to other tissues. NR supplementation did not further increase hepatic NAD biosynthetic genes. As shown in FIG. 11B, the lactating liver has a higher level of NAD than the nonlactating liver but it does not appear to hold on to a higher level of NR (FIG. 11C) or Nam (FIG. 11D), suggesting that lactation may lead to circulation of NAD precursors to the mammary.

Figure 12A:
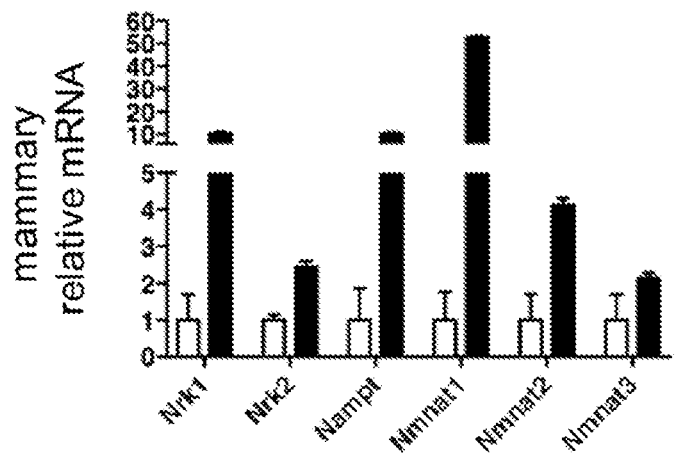
FIGS. 12A-D. Lactation and NR boost the mammary NAD program.
Figure 12B:
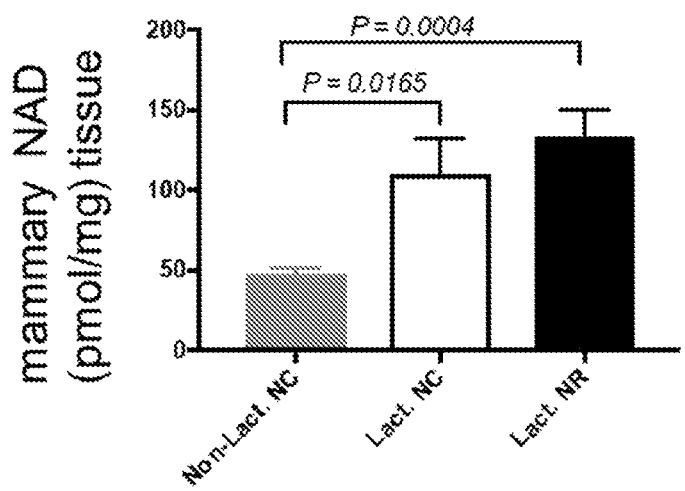
Figure 12C:
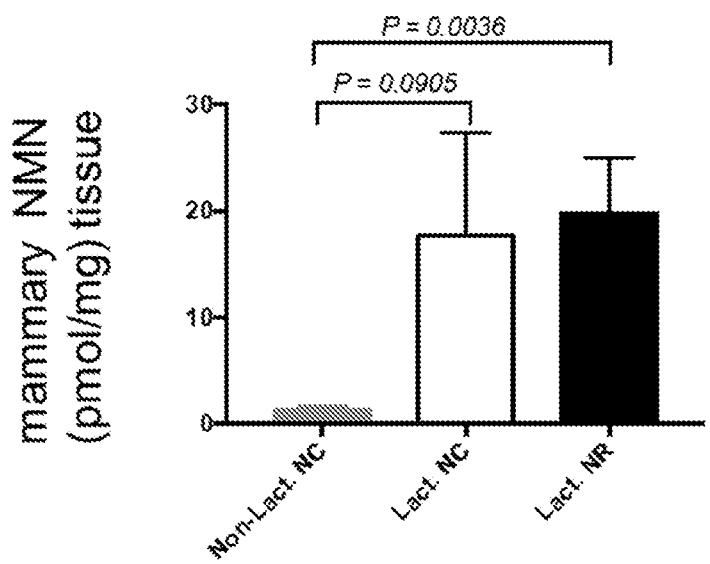
Figure 12D:
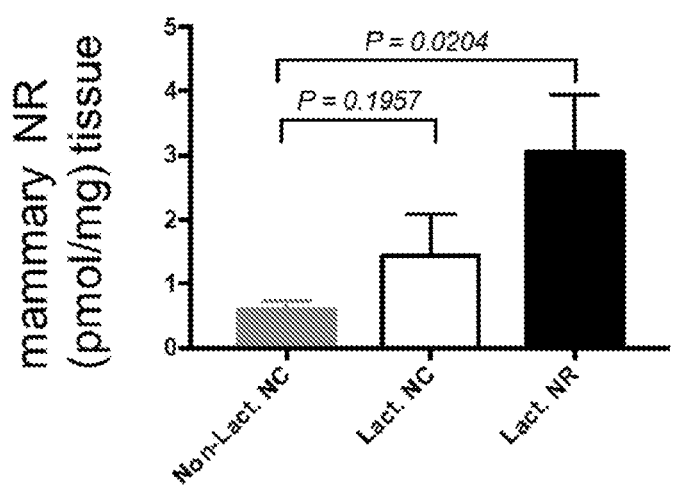

As shown in FIG. 12A, the lactating mammary in a mother supplemented with NR has a very high level of expression of NAD biosynthetic genes. As shown in FIGS. 12B-12C, maternal NAD and NMN are elevated in the mammary of lactating mammary with respect to nonlactating mammary tissue. As shown in FIG. 12D, maternal NR given to a lactating female mouse produces a large increase in mammary NR above the already elevated level of NR in the lactating female.

Example 5

Post-partum nicotinamide riboside boosts mammary biosynthetic programs.

Figure 13A:
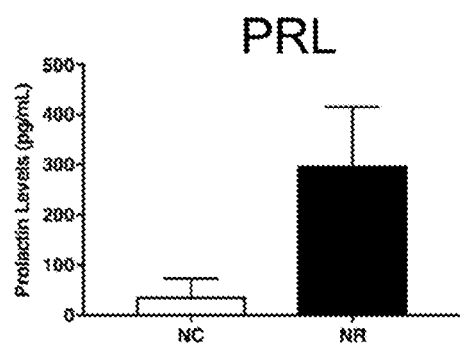
FIGS. 13A-D. NR boosts prolactin circulation and mammary biosynthetic pathways for protein, fat and carbohydrate.
Figure 13B:
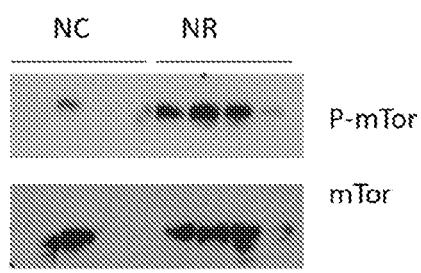
Figure 13C:
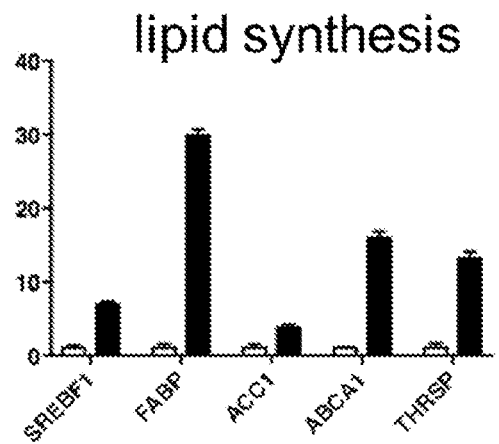
Figure 13D:
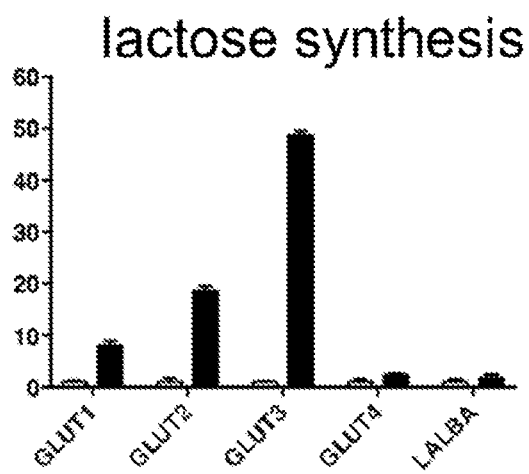
Figure 14A:
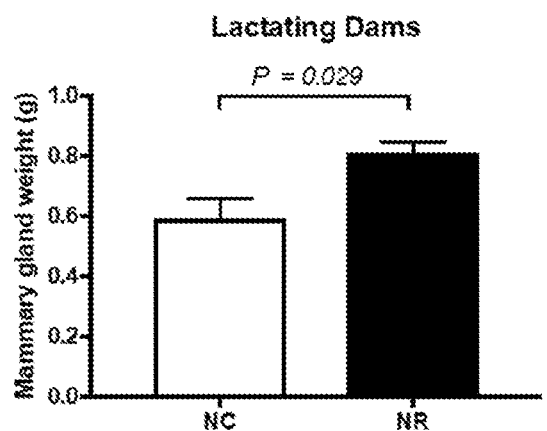
FIGS. 14A-B. Postpartum NR supplementation promotes mammary gland development (n=5 mice per group) (FIG. 14A). NR increases heat loss by increasing expression of UCP1 (FIG. 14B).
Figure 14B:
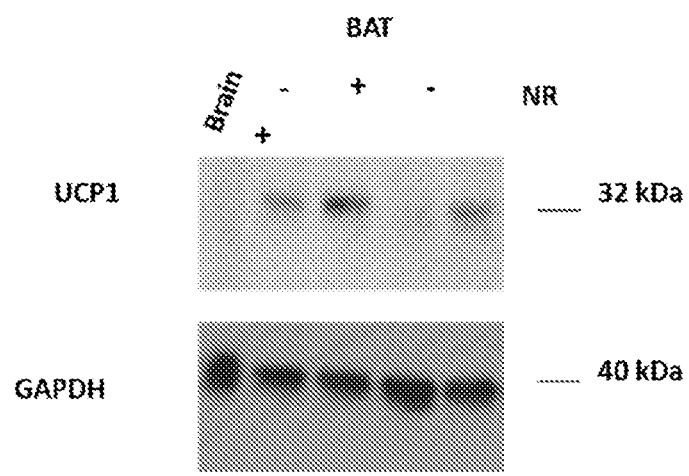

As shown in FIG. 13A, it was discovered that NR-supplemented mothers circulate very high levels of prolactin. Consistent with high level prolactin circulation and high level milk production, as shown in FIG. 13B, there is a higher level of phosph-mTOR in mammary of NR-supplemented mothers to drive higher protein synthesis. As shown in FIG. 13C and 13D, mammary lipid biosynthetic genes and lactose biosynthetic genes are strongly induced by provision of NR in the diet. In addition, the size of the mammary tissue itself is greater in NR-supplemented mothers than in non-supplemented mothers (FIG. 14A). As shown in FIG. 14B, the mammary tissue from NC and NR-supplemented mothers was probed and it was discovered that NR-supplementation produces an increase in expression of UCP1, indicating that NR supplemented mothers may have both an advantage in weight loss from increased transmission of calories from milk as well as increased thermogenesis.

Example 6

Post-partum nicotinamide riboside increases neonatal health and development.

Figure 15:
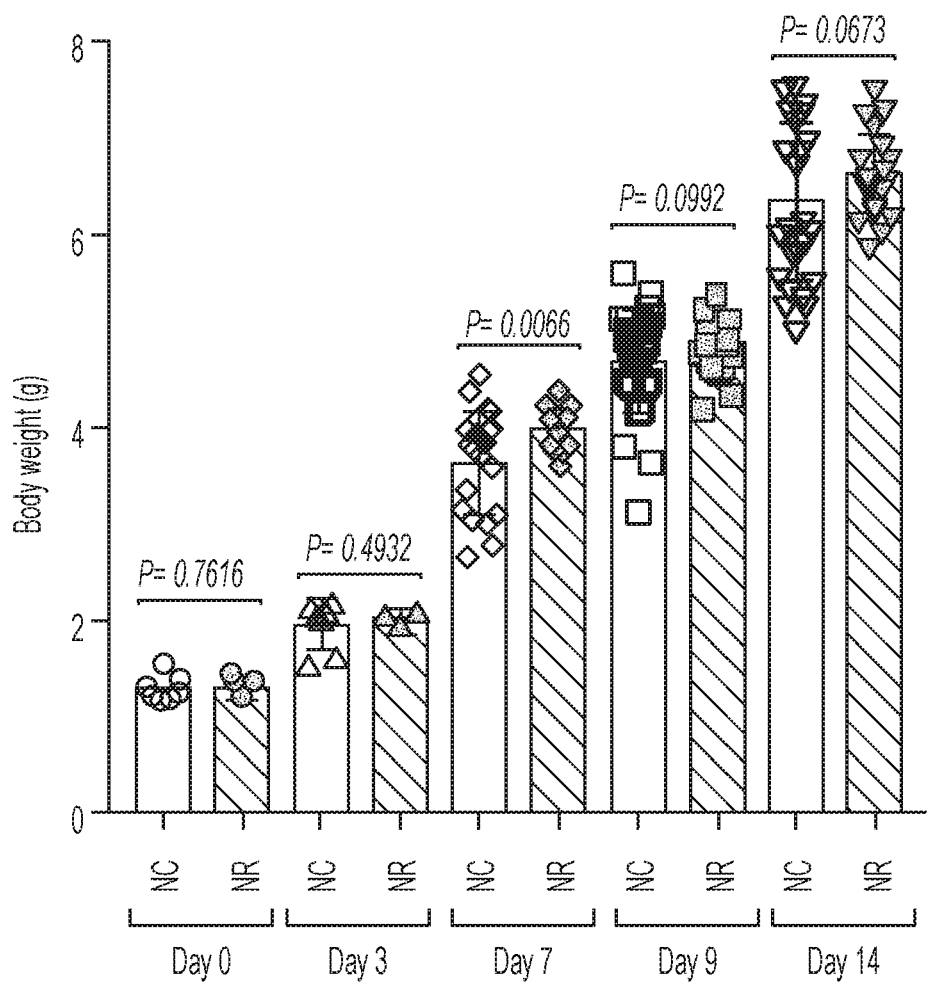
FIG. 15. Maternal NR increases pup growth early in the neonatal period. Neonatal pups body weight from Day 0 to Day 14 (n=5 litter per group).
Figure 16A:
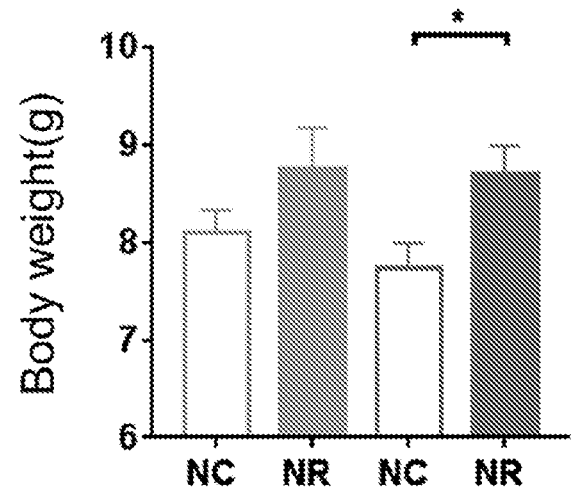
FIGS. 16A-D. 21 day old pups of NR-supplemented mothers are bigger. Males and females were analyzed separately. The order of the bars from left to right are: males of normal chow (NC) mothers (white with light grey outline), followed by males of NR-supplemented mothers (filled light grey), followed by females of NC mothers (white with dark grey outline), followed by females of NR-supplemented mothers (filled dark grey).
Figure 16B:
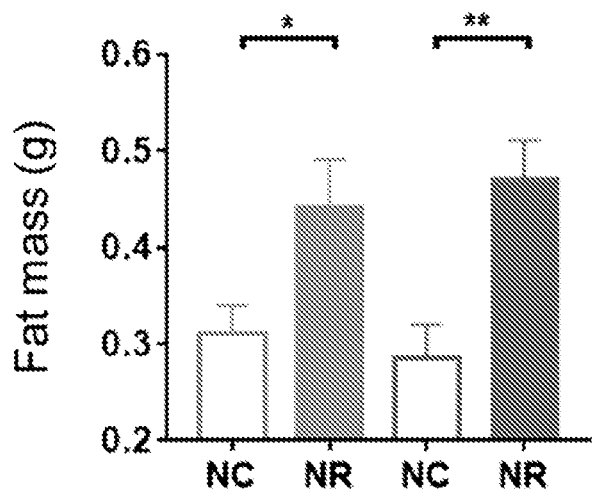
Figure 16C:
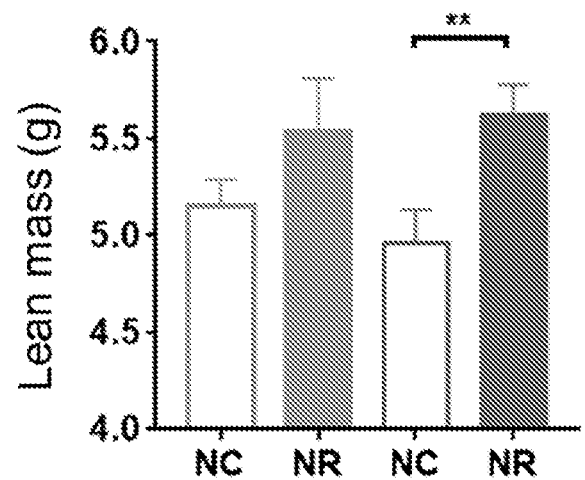
Figure 16D:
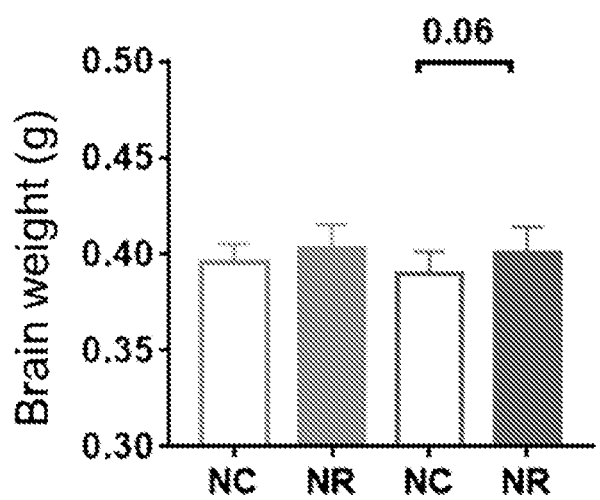

As shown in FIG. 15, particularly at day 7 and 9, the mother's NR supplementation boosts neonatal size. As shown in FIG. 16A-C, 21 day old weanlings of NR-supplemented mothers are larger in overall mass, fat mass and lean mass. As shown in FIG. 16D, females tend to have larger brain weight.

Figure 17A:
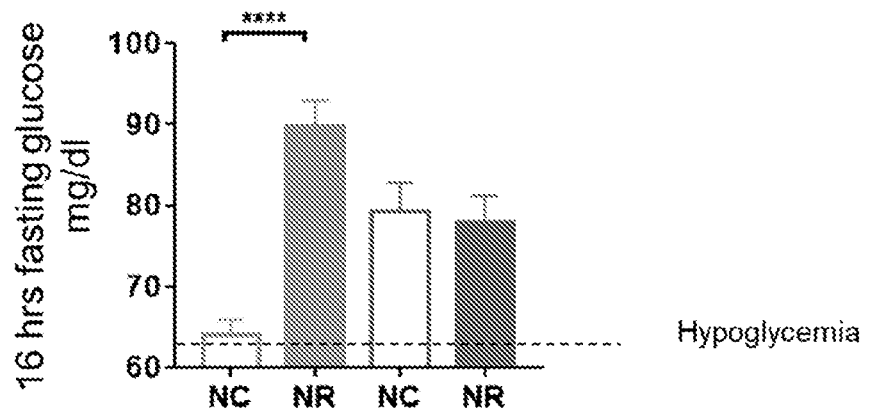
FIGS. 17A-C. 22 day old pups of NR-supplemented mothers have improved post-fasting glucose homoeostasis with higher gluconeogenic gene expression and higher hepatic glycogen storage. Not only are the offspring of NR-supplemented mothers a bit bigger, they also have better glycemic control. This is due to better gluconeogenic gene expression and higher glycogen storage. The order of the bars from left to right are: males of normal chow (NC) mothers (white with light grey outline), followed by males of NR-supplemented mothers (filled light grey), followed by females of NC mothers (white with dark grey outline), followed by females of NR-supplemented mothers (filled dark grey).
Figure 17B:
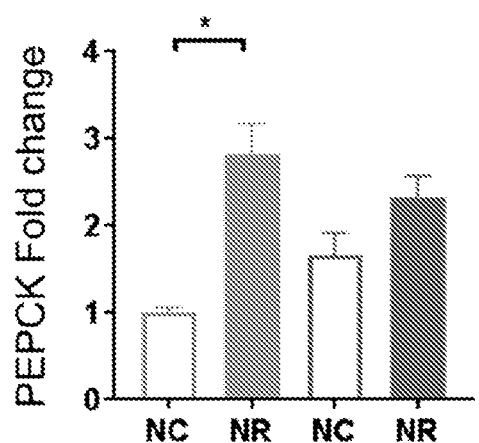
Figure 17C:
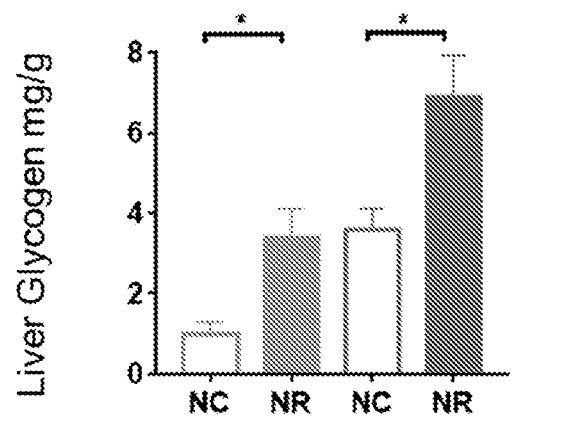

Earlier it was shown that supplementation of females during their pregnancy and during the lactation period with NR produced pups with better glycemic control. Here again, it was found that 15 day old males offspring of non-supplemented mothers could not maintain their blood glucose with a 16 hour fast. Furthermore, it was discovered that males and females whose mothers were NR-supplemented had higher liver expression of the gluconeogenic bypass gene, PEPCK (FIG. 17B), and stored more glycogen in their livers (FIG. 17C). Particularly as NR is not directly transmitted to offspring of NR-supplemented mothers, none of these effects of maternally supplemented NR could have been anticipated.

Example 7

Post-partum nicotinamide riboside produces profound, lasting effects on the activity, anti-anxiety, adventurousness and physical abilities of offspring.

Figure 18A:
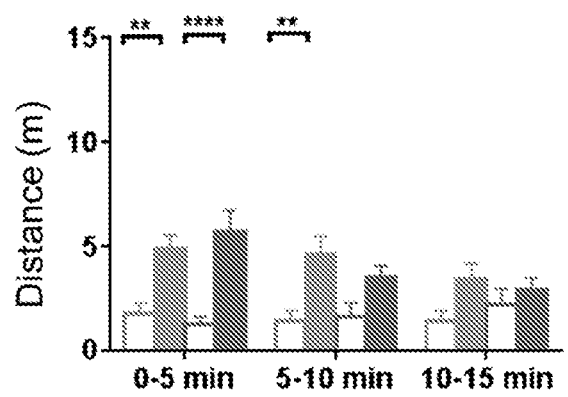
FIGS. 18A-B. Mother's NR supplementation produces adventurous neonatal offspring: 15 day old pups of NR-supplemented mothers cover more distance in an open field test and males also spend more time in the center. The order of the bars from left to right are: males of normal chow (NC) mothers (white with light grey outline), followed by males of NR-supplemented mothers (filled light grey), followed by females of NC mothers (white with dark grey outline), followed by females of NR-supplemented mothers (filled dark grey).
Figure 18B:
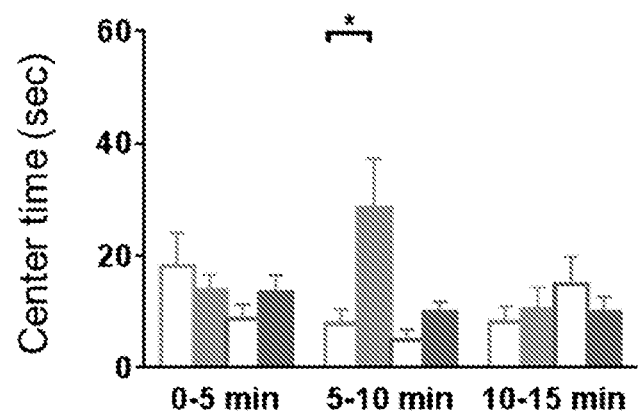
Figure 19A:
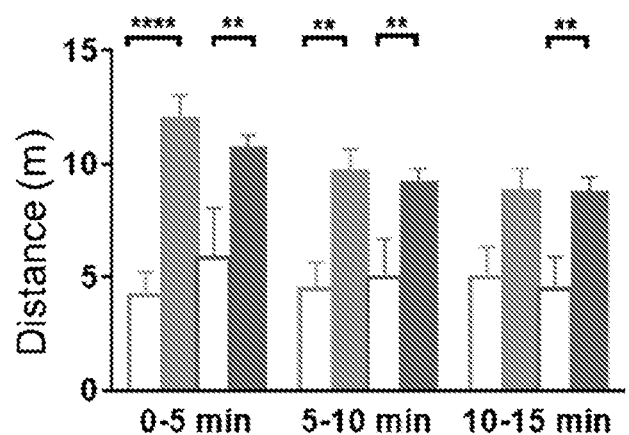
FIGS. 19A-D. 49 days after their mother's intervention, 70 day-old adults of NR-supplemented mothers cover more distance and move faster in an open field test with a tendency toward less immobile time. Males spend less time in the center. These adults were treated identically ever since weaning. The only difference is whether the mother was NR-supplemented for 21 days. They are faster and more adventurous. The order of the bars from left to right are: males of normal chow (NC) mothers (white with light grey outline), followed by males of NR-supplemented mothers (filled light grey), followed by females of NC mothers (white with dark grey outline), followed by females of NR-supplemented mothers (filled dark grey).
Figure 19B:
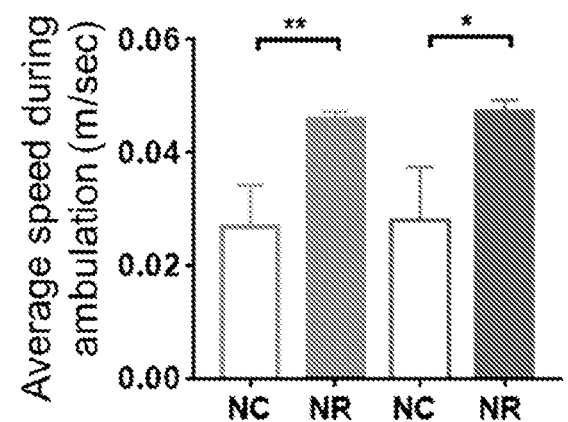
Figure 19C:
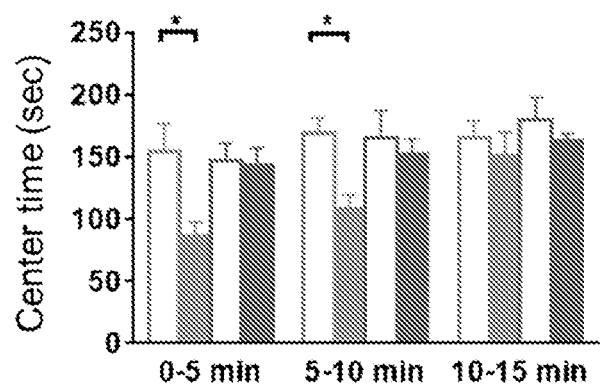
Figure 19D:
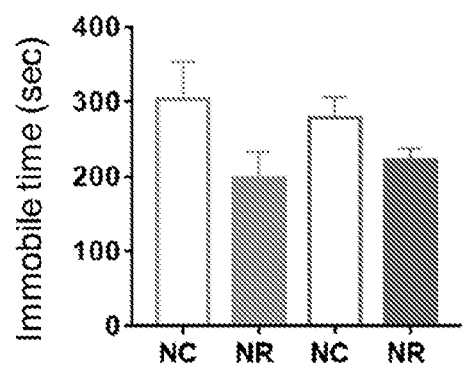

At 15 days of age, it was observed that the offspring of NR-supplemented mothers were more physically active. In this experiment, the physical activity of male and female offspring of mothers supplemented or not with NR at 15 days of age was quantified. Particularly in the first 5 minutes in which they were introduced into the open field test, the offspring of NR-supplemented mothers were much more physically active than those of control 15 day old mice (FIG. 18A). The males were also willing to spend a significant amount of time in the center of the open field test in the middle 5 minute epoch (FIG. 18B), suggesting that they were not anxious.

At 21 days, the offspring were removed from their mothers and put on normal chow (NR). While offspring of NR could have been put on NR chow, we aimed to determine if the 21 day intervention to their mothers was sufficient for a lasting effect on their neurocognitive and/or physical development. As shown in FIGS. 19A-D, 49 days after their mother's intervention, 70 day-old adults of NR-supplemented mothers cover more distance and move faster in an open field test with a tendency toward less immobile time. Males spend less time in the center.

Figure 20A:
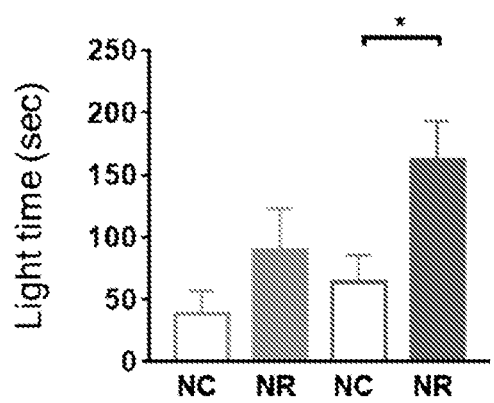
FIGS. 20A-C. 54 days after their mother's intervention, 75 day-old female offspring of NR-supplemented mother spend more time in the light (e.g., have reduced anxiety and are less fearful). The order of the bars from left to right are: males of normal chow (NC) mothers (white with light grey outline), followed by males of NR-supplemented mothers (filled light grey), followed by females of NC mothers (white with dark grey outline), followed by females of NR-supplemented mothers (filled dark grey).
Figure 20B:
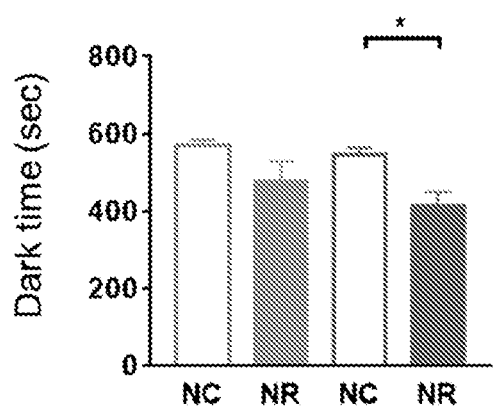
Figure 20C:
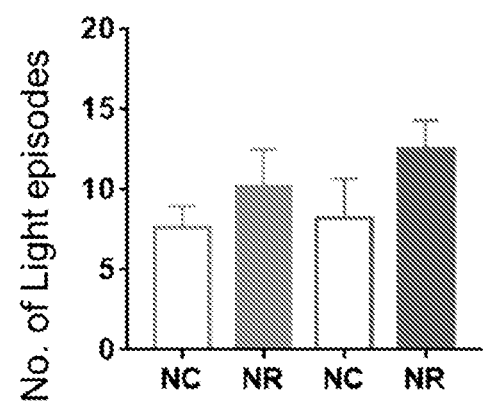

It was considered interesting that males and female adults of NR-supplemented mothers maintain distinct physical advantages into adulthood on the basis of the mother's micronutrition. At 75 days of age-54 days after the mothers either had NR or not—the offspring of NR-supplemented mothers were more willing to spend time in the light chamber of a dark/light chamber (FIG. 20). This could be interpreted either as a simple increase in activity and/or a less anxious state of being.

Just as the male adults of NR-supplemented mothers had a lasting and statistically significant advantage over genetically identical mice whose mothers were not supplemented, the female mice of NR-supplemented mothers showed other statistically significant demonstrable benefits.

Figure 21A:
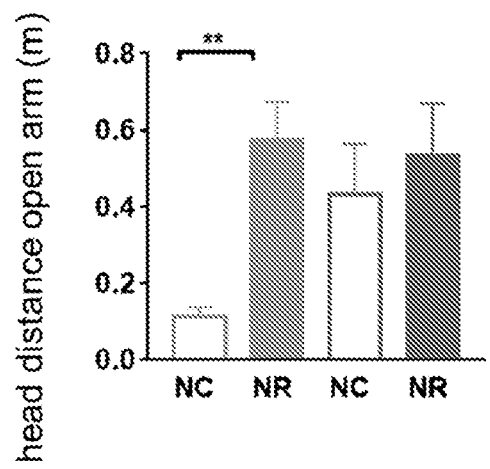
FIGS. 21A-B. 64 days after their mother's intervention, 85-day-old male offspring of NR-supplemented mothers exhibit less anxiety on an elevated plus maze. Males are not afraid to "stick their head out". The order of the bars from left to right are: males of normal chow (NC) mothers (white with light grey outline), followed by males of NR-supplemented mothers (filled light grey), followed by females of NC mothers (white with dark grey outline), followed by females of NR-supplemented mothers (filled dark grey).
Figure 21B:
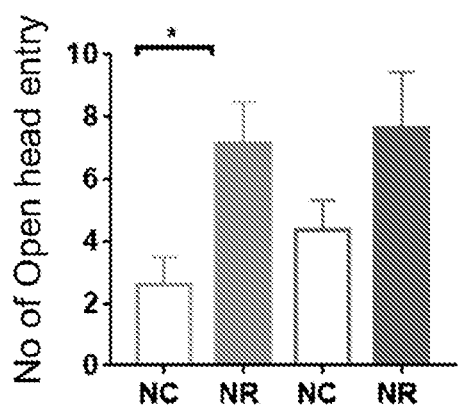

At 64 days past the mother's intervention, the willingness of 85 day old adult offspring of mice from this experiment (NC or NR-supplemented) to put their heads out in an elevated plus maze was tested. In a clear indication of anti-anxiety, as shown in FIGS. 21A-B, the offspring of NR-supplemented mothers had a higher willingness to do this and the propensity to do this of the males of NR-supplemented mothers easily reached statistical significance. The clear indication is that maternal NR produces improvements in maternal behavior and/or qualitative and/or quantitative improvements in lactation sufficient to improve the development and health of offspring. The ability of the mother's 21 day micronutrition to produce beneficial effects on her offspring into adulthood was not at all anticipated.

Figure 22A:
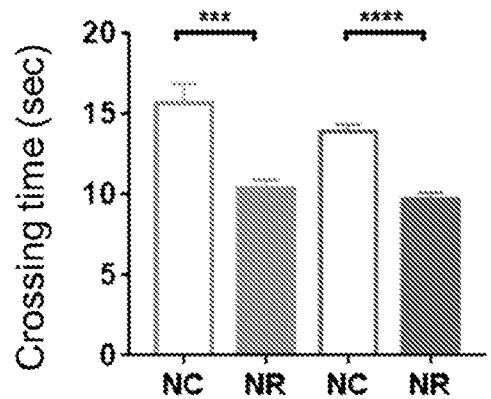
FIGS. 22A-C. 64 days after their mother's intervention, 85-day-old adults of NR-supplemented mothers have better performance on a balance beam. They cross a beam balance faster (untrained); they slip fewer times; and they almost never grip the beam with their tail. Overall, these mice are more coordinated and are superior physical specimens. The order of the bars from left to right are: males of normal chow (NC) mothers (white with light grey outline), followed by males of NR-supplemented mothers (filled light grey), followed by females of NC mothers (white with dark grey outline), followed by females of NR-supplemented mothers (filled dark grey).
Figure 22B:
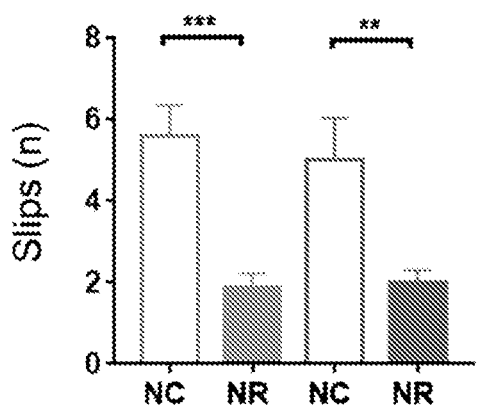
Figure 22C:
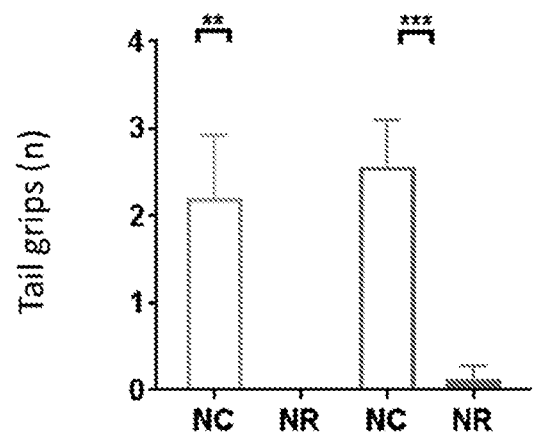

The improved physical functions of adult offspring of NR-supplemented mothers were not confined to advantages in making less anxious choices about where to move in space, light and dark. At 85 days old, when mice were again 64 days past their mother's intervention—again all mice were on NC show for 64 days—their untrained ability to cross a balance beam was tested. As shown in FIGS. 22A-C, the male and female offspring of NR-supplemented mothers cross faster, with fewer slips and with virtually no use of their tails to grip the balance beam. This was not anticipated.

Figure 23A:
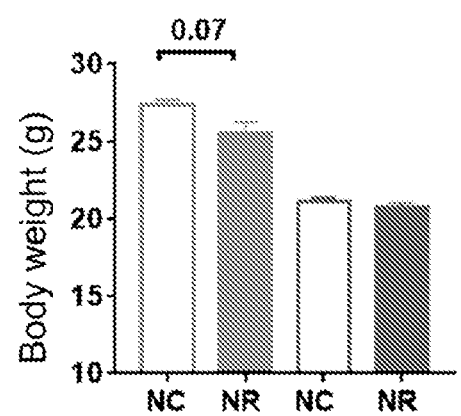
FIGS. 23A-C. 69 days after their mother's intervention, 90 day-old adult offspring of NR-supplemented mothers have less fat mass. The order of the bars from left to right are: males of normal chow (NC) mothers (white with light grey outline), followed by males of NR-supplemented mothers (filled light grey), followed by females of NC mothers (white with dark grey outline), followed by females of NR-supplemented mothers (filled dark grey).
Figure 23B:
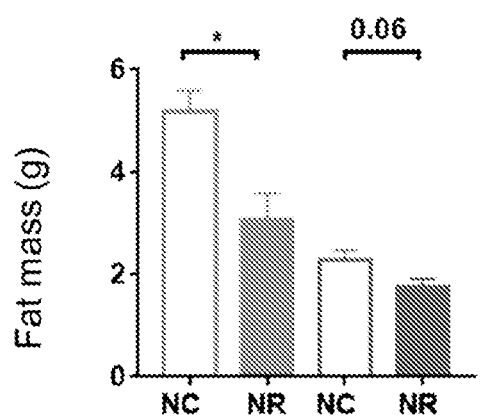
Figure 23C:
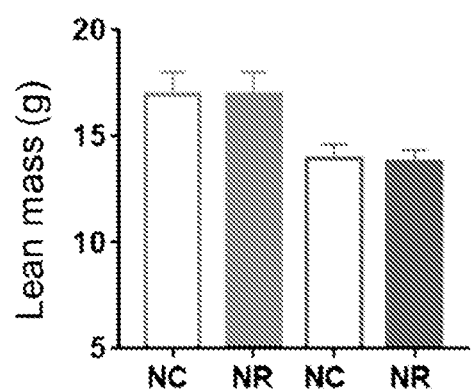

At 90 days old, body composition analysis was performed on the mice. As shown in FIGS. 23A-C, the male offspring of NR-supplemented mothers were slightly smaller. As shown in FIG. 23B, males and females of NR-supplemented mothers have less adipose tissue 69 days after their mother's intervention. There is no effect on the total amount of lean mass (23C). Particularly because the maternal intervention produced somewhat bigger weanlings with more fat and lean mass, the protection against age-induced weight gain was unanticipated.

Figure 24A:
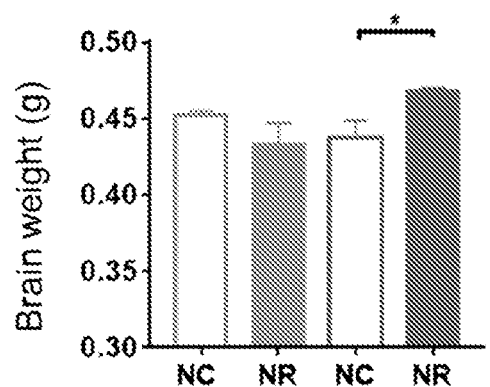
FIGS. 24A-D. 69 days after their mother's intervention, the female offspring tend to have larger brains (statistically significant) (FIG. 24A). Pups of NR-supplemented moms show advanced pruning of the caudate putamen at day 22 (FIGS. 24B-C); however, the caudate putamen in pups from NR-supplemented mothers grows to a normal size in adulthood (FIG. 24D). The order of the bars from left to right are: males of normal chow (NC) mothers (white with light grey outline), followed by males of NR-supplemented mothers (filled light grey), followed by females of NC mothers (white with dark grey outline), followed by females of NR-supplemented mothers (filled dark grey).
Figure 24B:
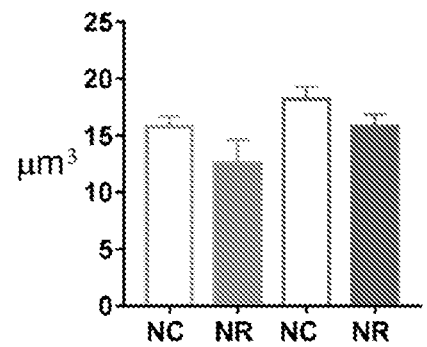
Figure 24C:
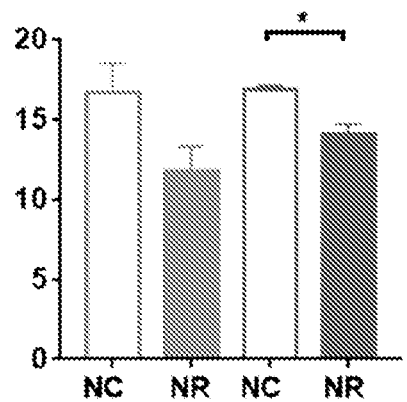
Figure 24D:
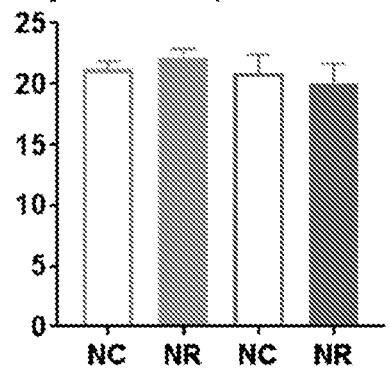

At 91 days, the mice were sacrificed and examined with respect to their brains. In FIG. 24A, it was shown that female mice from NR-supplemented mothers have larger brains in adulthood. We hypothesized that the caudate putamen, which is the motor learning center of the brain, may have developed more rapidly in mice whose mothers had been NR-supplemented either due to the increased quality and/or quantity of milk they received and/or improved maternal care. The caudate putamen was slightly smaller for weanlings of NR-supplemented mothers at 21 days (FIG. 24B) and showed clearly advanced pruning in females as evidenced by a smaller and more focused area of PSD95 staining (FIG. 24C). As shown in FIG. 24D, the caudate putamen in adults was not affected, indicating that the effect of NR-supplementation is to advance neonatal pruning and not to stunt brain growth.

Certain unanticipated activities of maternal NR supplementation on maternal and neonatal health are described below.

Maternal Weight Loss

Here, it is shown that NR has the unexpected property of a galactogogue, i.e., it stimulates lactation. As described herein, it was shown that NR boosts mammary biosynthetic programs and further that NR allows lactating females to produce larger mammary glands with a greater degree of UCP1 expression. As shown in FIGS. 1 and 6, mouse mothers on NR had a significant advantage in post-partum weight management with preservation of their lean mass. The observations and mechanisms of post-partum weight management were unexpected and possess significant commercial and translational potential.

Neonatal Metabolic and Whole Body Development of Offspring from NR-supplemented Mothers Because of the remarkable ability of NR to promote maternal lactation, the ability of offspring of NR-supplemented mothers to maintain fasting euglycemia was examined. The data indicated that the mother's NR supplementation protects mice from low blood sugar after an overnight fast. Specifically, it was discovered that the offspring of NR-supplemented offspring grow somewhat faster, have better hepatic gluconeogenic gene expression, store more glucose, and can be somewhat larger at weaning. Because normal mouse chow is not deficient in any micronutrients, none of these effects could have been foreseen.

Neurocognitive and Physical Development of Offspring from NR-supplemented Mothers At 15 days, mice are able to open their eyes. By 30 days, mice are generally considered adults. It was consistently found that the offspring of NR-supplemented mice were advanced, adventurous, non-anxious and physically superior specimens from 15 days all the way to adulthood at 3 months of age. None of these observations could have been anticipated based on known activities of NR. Moreover, the effects are not due to NR itself but rather the effect of NR on maternal milk production and/or behavior. It was shown that the mother's oral NR is not directly transmitted to her offspring. She does produce more milk than non-supplemented mothers and may also transmit more time or more quality maternal caretaking time on the basis of her NR supplementation. Strikingly, NR caused lactating mice to produce more BDNF. The increased volume of milk coupled with increased concentration of BDNF and potentially other neuroactive substances in the milk has the potential to promote advanced pruning in the caudate putamen, giving rise to greater physical prowess. We further propose that the quality of milk in NR-supplemented mothers promotes advanced brain development, anti-anxiety and increased physical performance that lasts into adulthood.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method comprising, a) reducing pregnancy associated weight gain in a female human, by administering, pre-pregnancy or during pregnancy, an effective amount of a nicotinamide adenine dinucleotide (NAD) precursor to the female human, and/or b) promoting post-pregnancy weight loss in a female human by administering, during pregnancy or post pregnancy, a nicotinamide adenine dinucleotide (NAD) precursor to the female human; and
measuring pregnancy associated weight gain in the female human or measuring post-pregnancy weight loss in the female human.

2. A method comprising, increasing milk production in a female human that is lactating by administering, during pregnancy or after pregnancy, an effective amount of a nicotinamide adenine dinucleotide (NAD) precursor to the female human; and
measuring milk production in the female human.

3. The method of claim 1, comprising reducing pregnancy associated weight gain in the female human, by administering, pre-pregnancy or during pregnancy, a nicotinamide adenine dinucleotide (NAD) precursor to the female human; and
measuring pregnancy associated weight gain in the female human.

4. The method of claim 3, wherein the nicotinamide adenine dinucleotide (NAD) precursor is administered to the female human pre-pregnancy.

5. The method of claim 3, wherein the nicotinamide adenine dinucleotide (NAD) precursor is administered to the female human during pregnancy.

6. The method of claim 1, comprising promoting post-pregnancy weight loss in the female human by administering, pre-pregnancy or during pregnancy, a nicotinamide adenine dinucleotide (NAD) precursor to the female human; and
measuring post-pregnancy weight loss in the female human.

7. The method of claim 6, wherein the nicotinamide adenine dinucleotide (NAD) precursor is administered to the female human pre-pregnancy.

8. The method of claim 6, wherein the nicotinamide adenine dinucleotide (NAD) precursor is administered to the female human during pregnancy.

9. The method of claim 2, wherein the nicotinamide adenine dinucleotide (NAD) precursor is administered to the female human during pregnancy.

10. The method of claim 2, wherein the nicotinamide adenine dinucleotide (NAD) precursor is administered to the female human after pregnancy.

11. The method of claim 2, wherein the NAD precursor is a compound of formula (I):

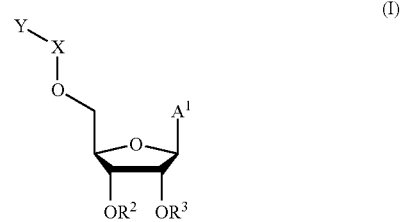

or a pharmaceutically acceptable salt thereof, wherein:

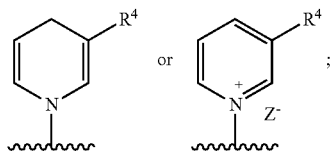

A¹ is

R¹ is —COOH, —C(=O)NH₂ or —C(=O)OR$^a$;

R² is H or (C₁-C₃)alkanoyl;

R³ is H or (C₁-C₃)alkanoyl;

i) X is absent, —P(=O)(OW)(O—), or —P(=O)(OW)—O—P(=O)(OW)(O—); and
   Y is W, or

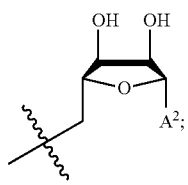

or ii) X is absent; and Y is (C₁-C₁₀)alkanoyl;

R$^a$ is (C₁-C₁₀)alkyl, (C₂-C₁₀)alkenyl, or aryl, wherein each (C₁-C₁₀)alkyl, (C₂-C₁₀)alkenyl and aryl is optionally substitutes with one or more groups independently selected from the group consisting of halo, hydroxyl, cyano, (C₁-C₃)alkoxy, (C₁-C₃)alkoxycarbonyl, aryl, and (C₁-C₃)alkanoyloxy;

each W is independently selected from the group consisting of H and pharmaceutically acceptable cations;

A¹ is

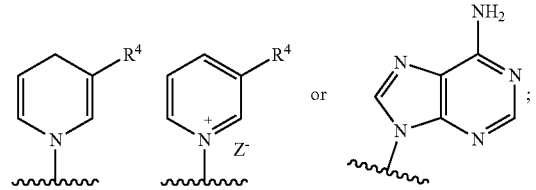

Z is a pharmaceutically acceptable anion;

R⁴ is —COOH, —C(=O)NH₂ or —C(=O)OR$^b$; and

R$^b$ is (C₁-C₁₀)alkyl, (C₂-C₁₀)alkenyl, or aryl, wherein each (C₁-C₁₀)alkyl, (C₂-C₁₀)alkenyl and aryl is optionally substitutes with one or more groups independently selected from the group consisting of halo, hydroxyl, cyano, (C₁-C₃)alkoxy, (C₁-C₃)alkoxycarbonyl, aryl, and (C₁-C₃)alkanoyloxy.

12. The method of claim 11, wherein the compound of formula (I) or the pharmaceutically acceptable salt thereof is selected from the group consisting of:

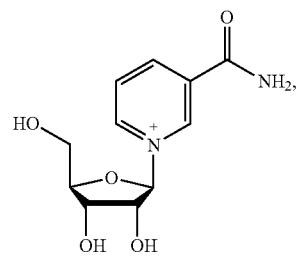

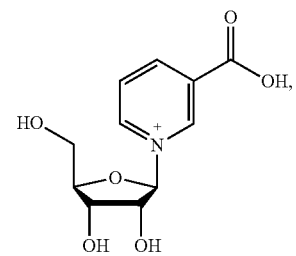

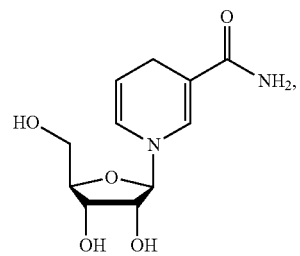

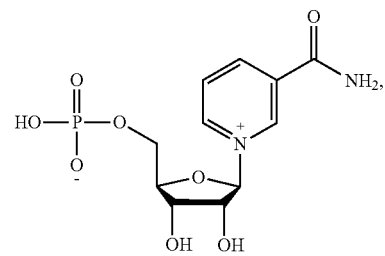

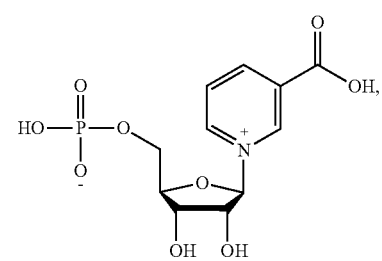

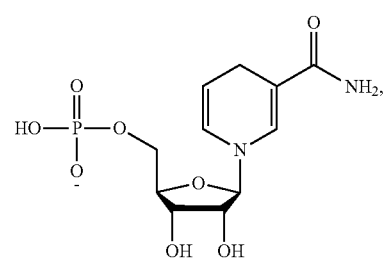

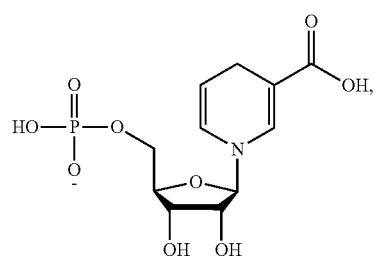
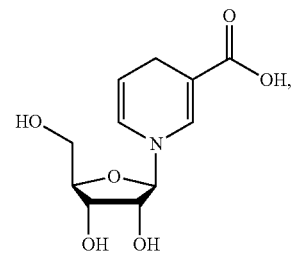
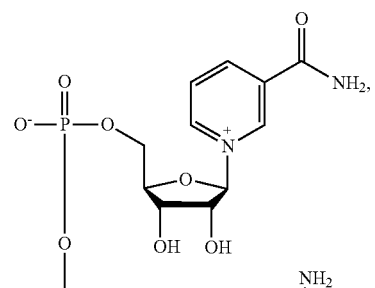
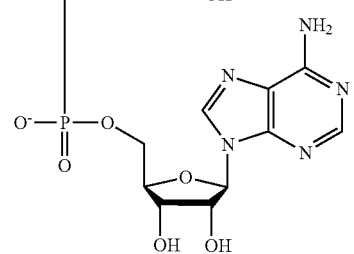
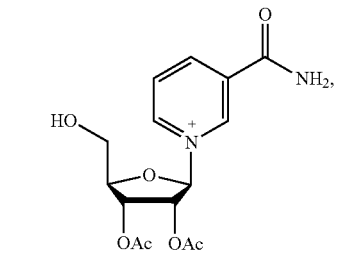
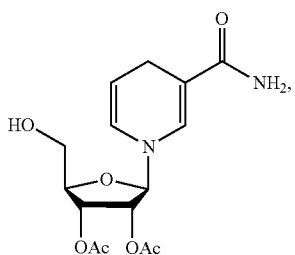
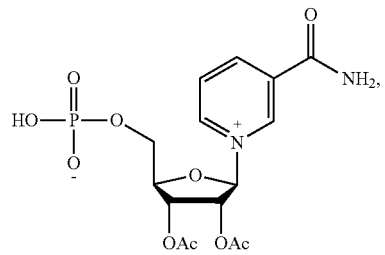
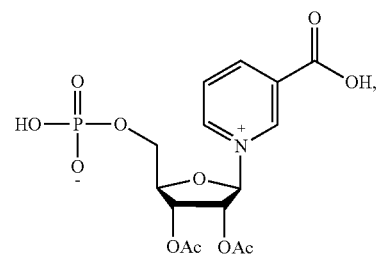
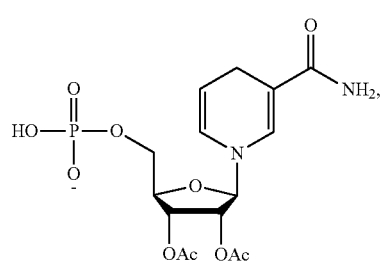
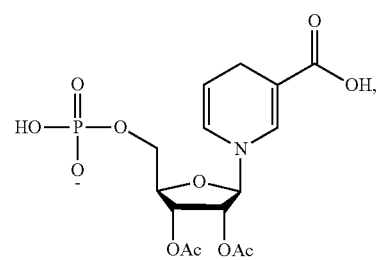
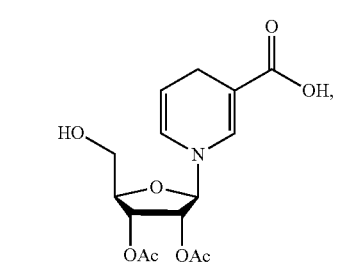

-continued
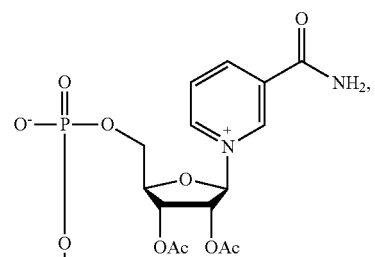
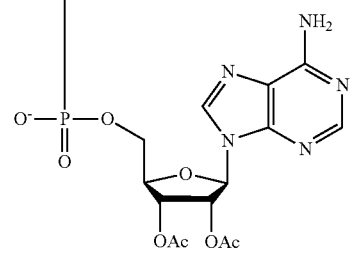
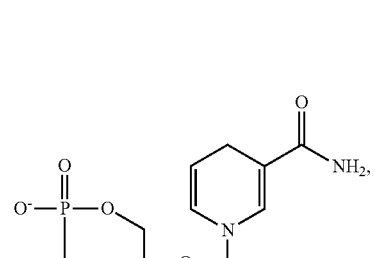
-continued
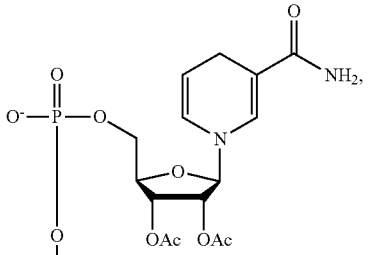
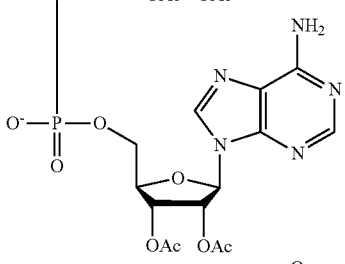
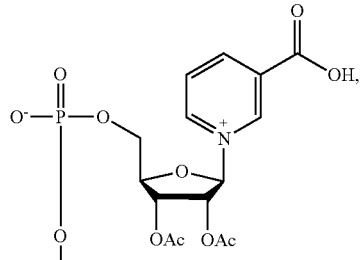
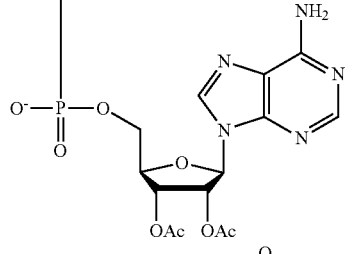
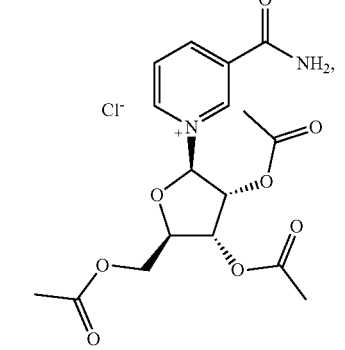
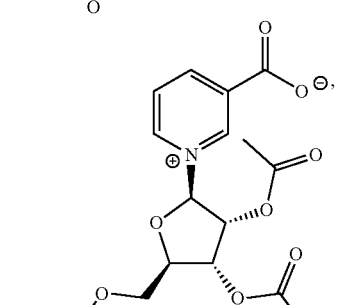

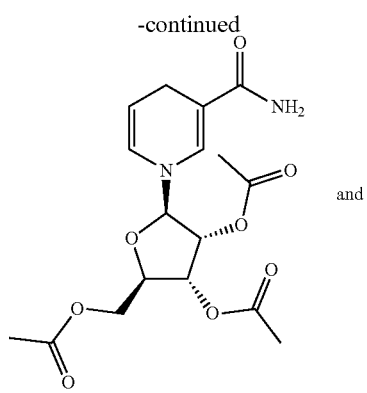

and pharmaceutically acceptable salts thereof.

13. The method of claim 3, wherein the NAD precursor is a compound of formula (I):

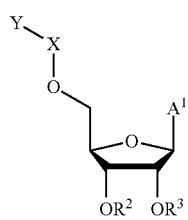

(I)

or a pharmaceutically acceptable salt thereof, wherein:
$A^1$ is

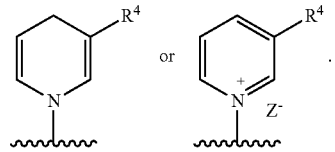

.

$R^1$ is —COOH, —C(=O)NH$_2$ or —C(=O)OR$^a$;
$R^2$ is H or (C$_1$-C$_3$)alkanoyl;
$R^3$ is H or (C$_1$-C$_3$)alkanoyl;
i) X is absent, —P(=O)(OW)(O—), or —P(=O)(OW)—O—P(=O)(OW)(O—); and
Y is W, or

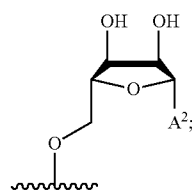

or
ii) X is absent; and Y is (C$_1$-C$_{10}$)alkanoyl;
$R^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;

each W is independently selected from the group consisting of H and pharmaceutically acceptable cations;
$A^2$ is

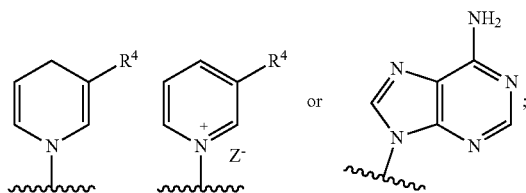

;

Z is a pharmaceutically acceptable anion;
$R^4$ is —COOH, —C(=O)NH$_2$ or —C(=O)OR$^b$; and
$R^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy.

14. The method of claim 13, wherein the compound of formula (I) or the pharmaceutically acceptable salt thereof is selected from the group consisting of:

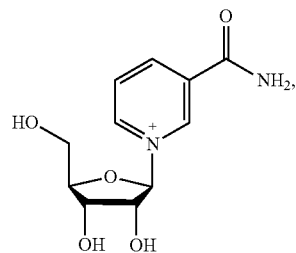

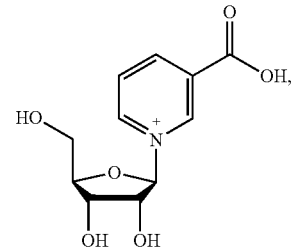

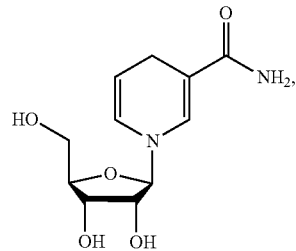

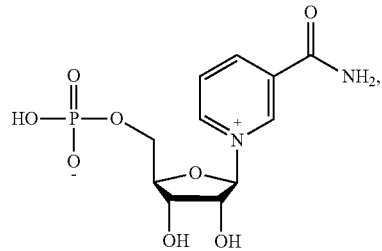

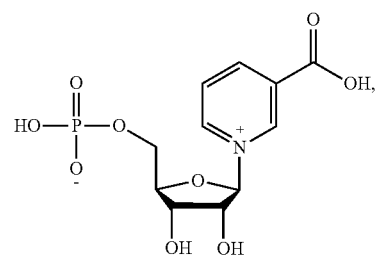
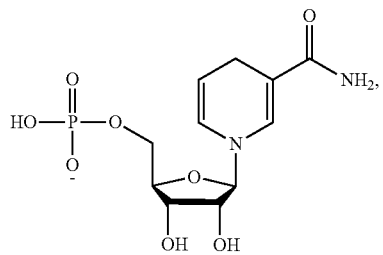
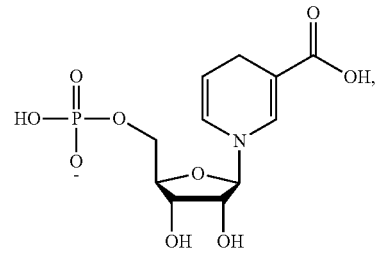
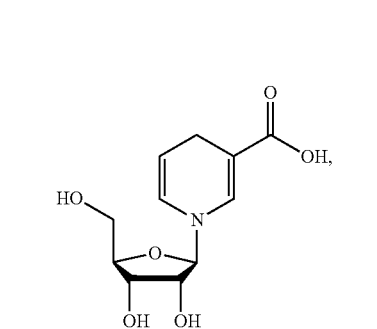
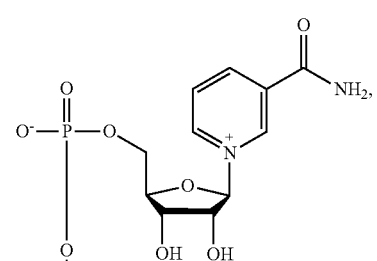
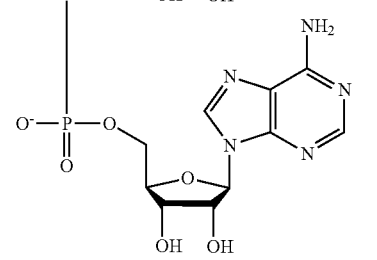
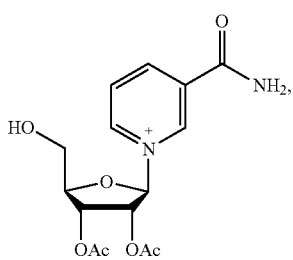
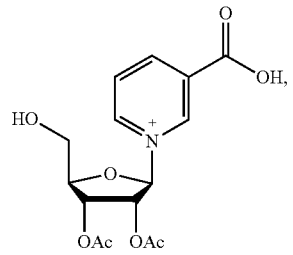
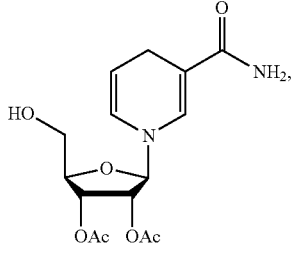
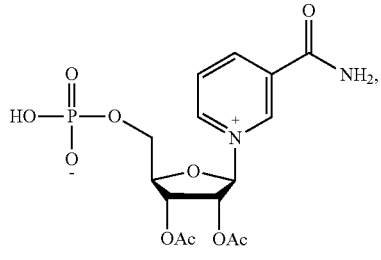
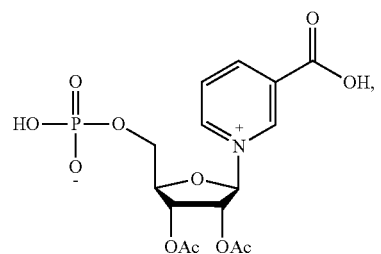
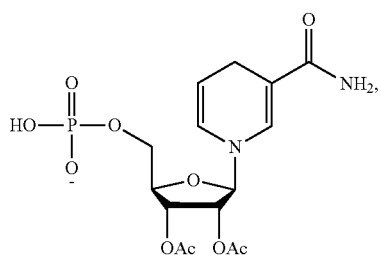

47
-continued
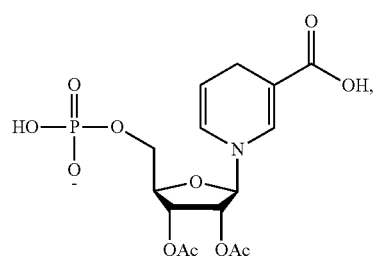
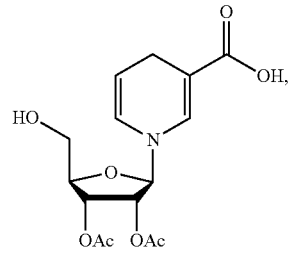
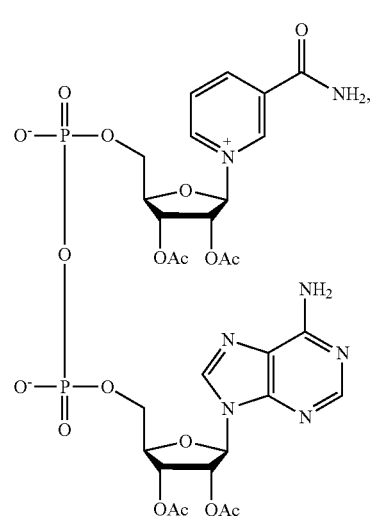
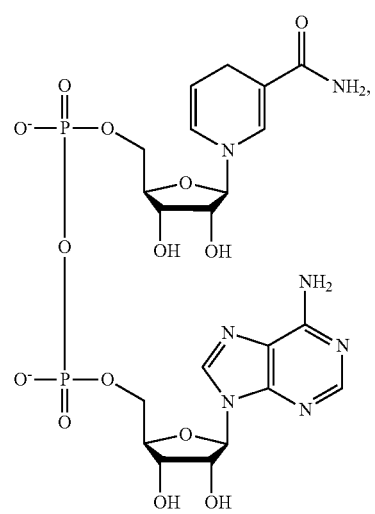
48
-continued
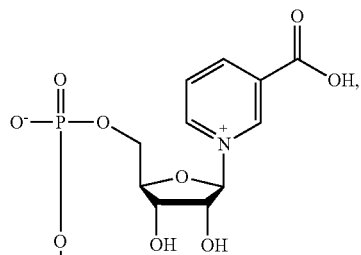
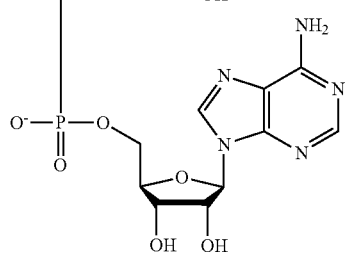
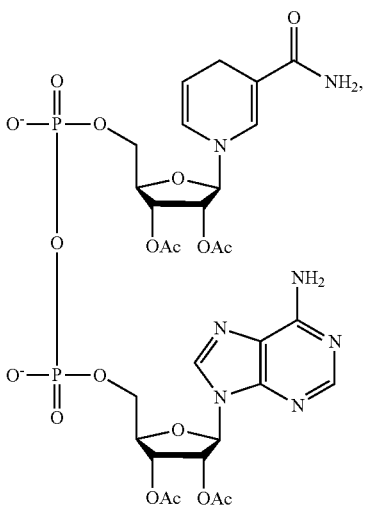
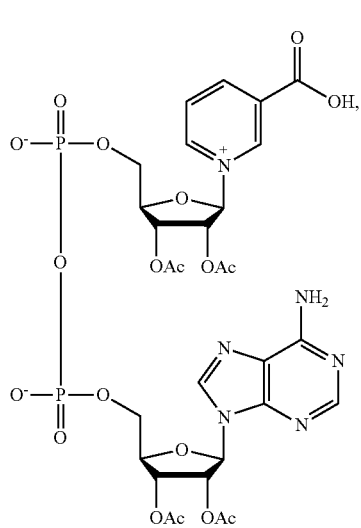

-continued

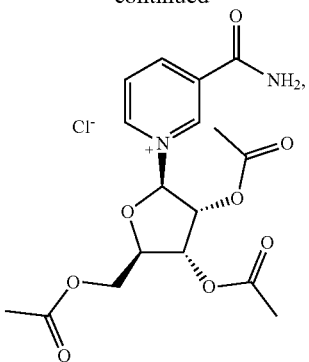

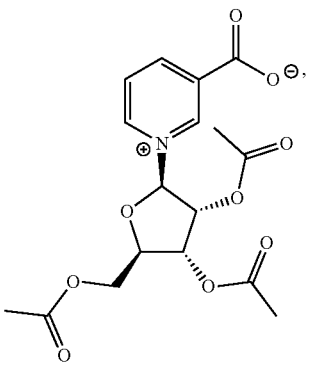

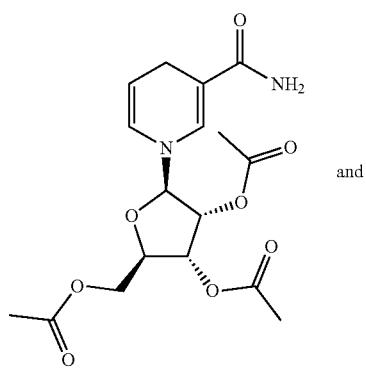

pharmaceutically acceptable salts thereof.

15. The method of claim 6, wherein the NAD precursor is a compound of formula (I):

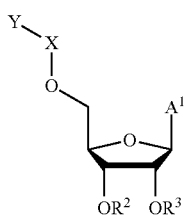
(I)

or a pharmaceutically acceptable salt thereof, wherein:

$A^1$ is

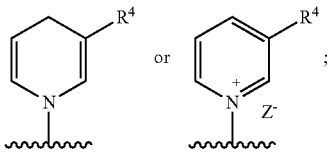

$R^1$ is —COOH, —C(=O)NH$_2$ or —C(=O)OR$^a$;

$R^2$ is H or (C$_1$-C$_3$)alkanoyl;

$R^3$ is H or (C$_1$-C$_3$)alkanoyl;

i) X is absent, —P(=O)(OW)(O—), or —P(=O)(OW)—O—P(=O)(OW)(O—); and

Y is W, or

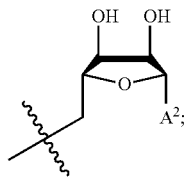

or ii) X is absent; and Y is (C$_1$-C$_{10}$)alkanoyl;

$R^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;

each W is independently selected from the group consisting of H and pharmaceutically acceptable cations;

$A^2$ is

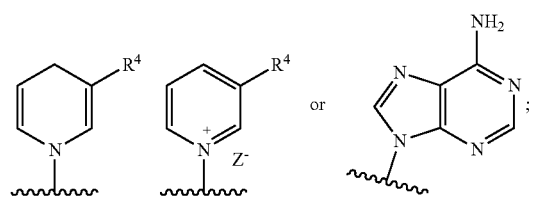

Z is a pharmaceutically acceptable anion;

$R^4$ is —COOH, —C(=O)NH$_2$ or —C(=O)OR$^b$; and $R^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy.

16. The method of claim 15, wherein the compound of formula (I) or the pharmaceutically acceptable salt thereof is selected from the group consisting of:

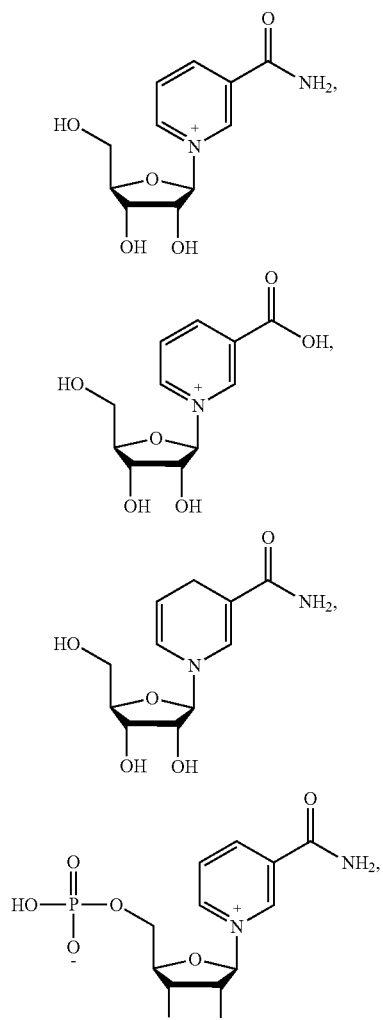
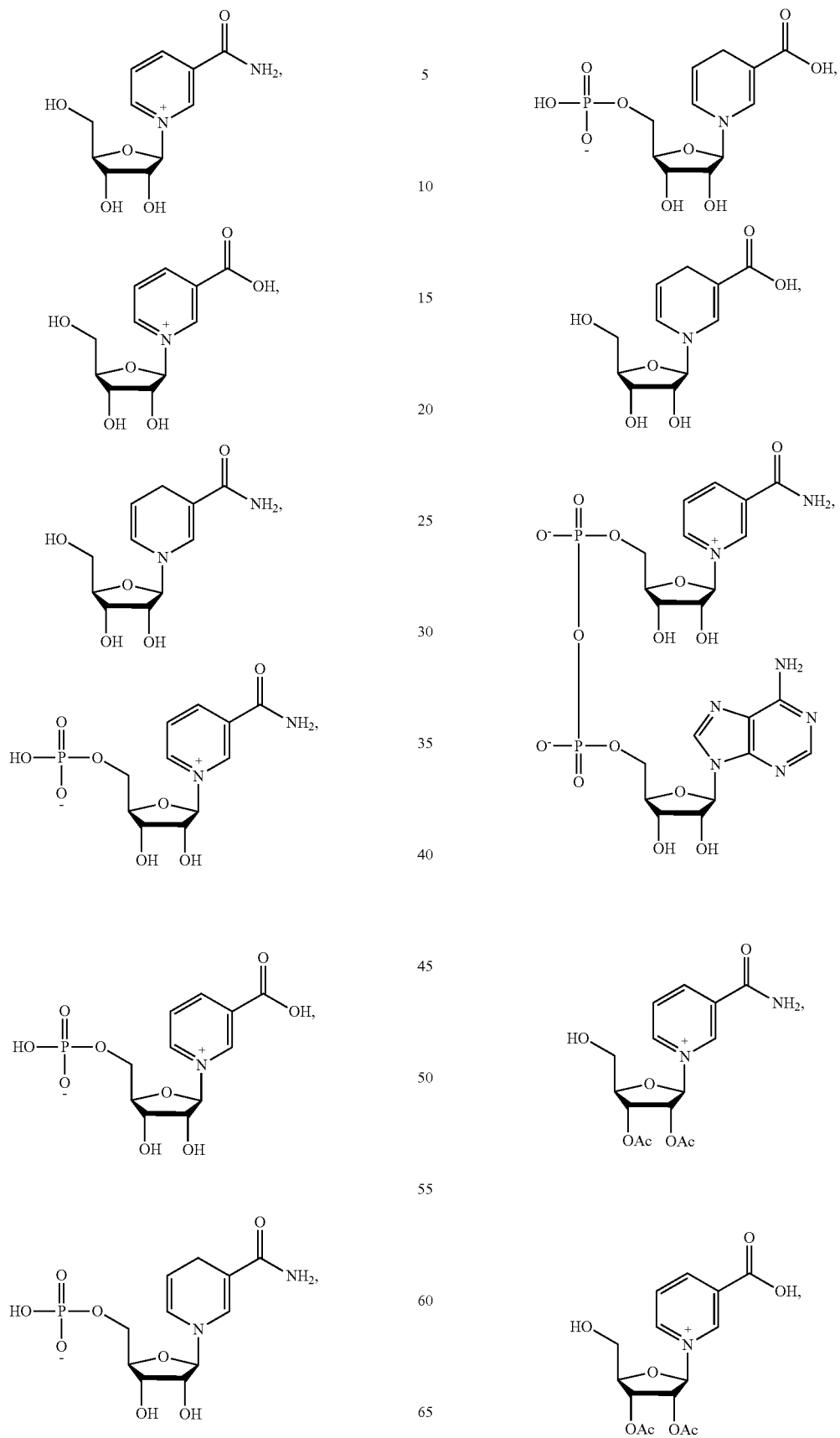
-continued

53
-continued
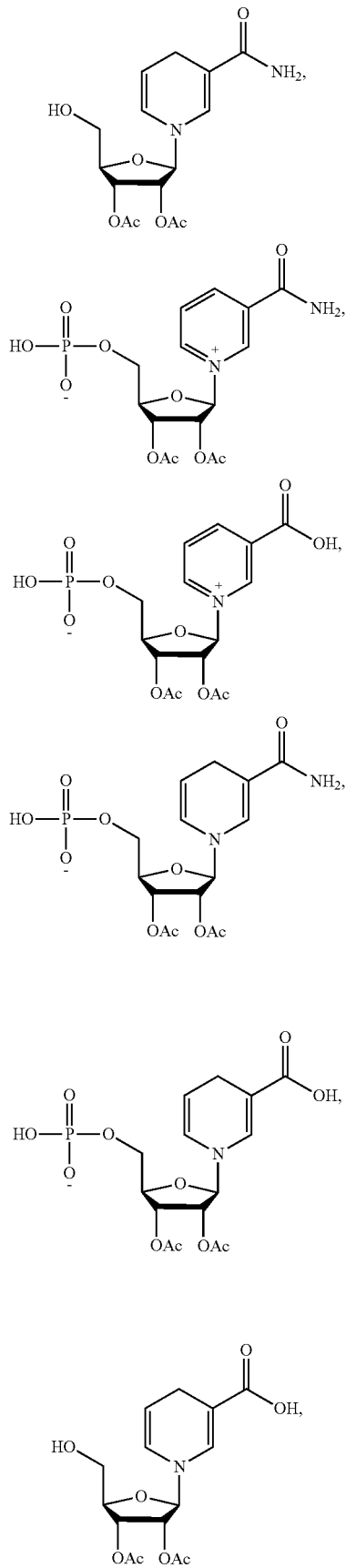
54
-continued
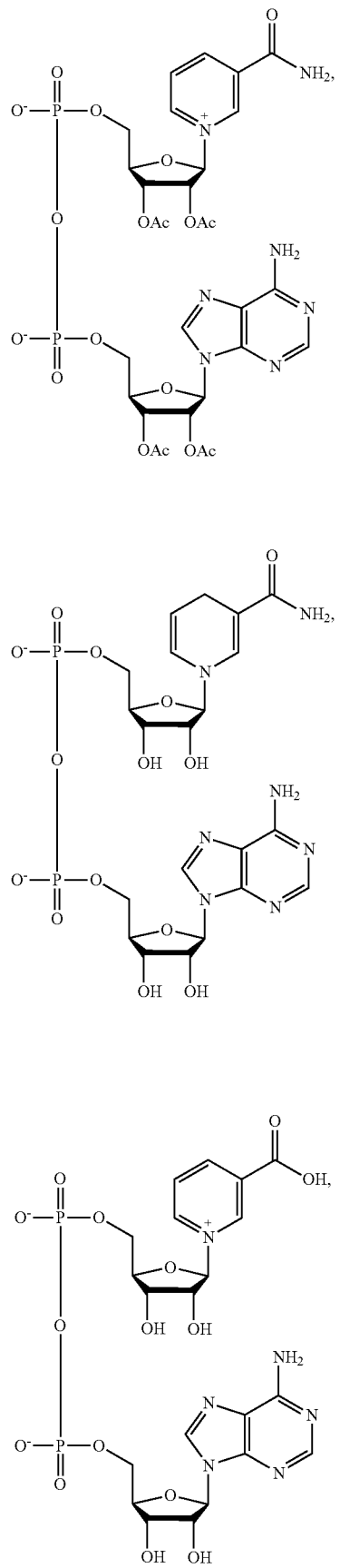

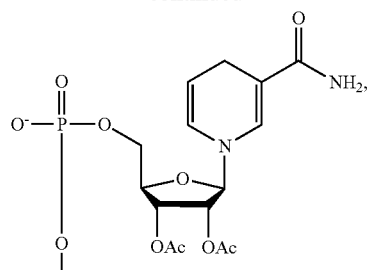
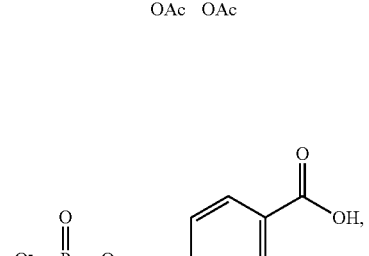
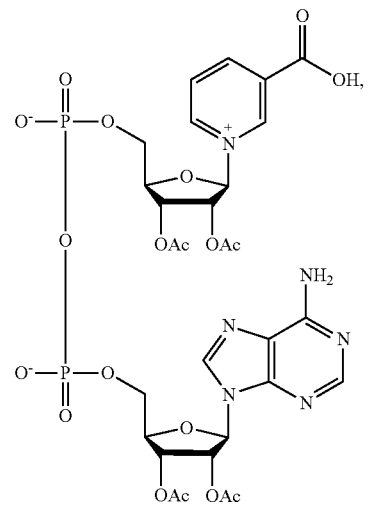
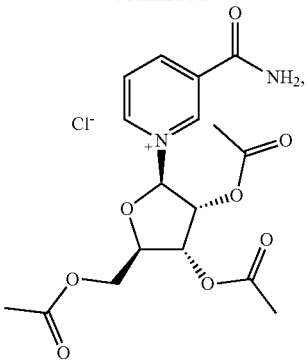
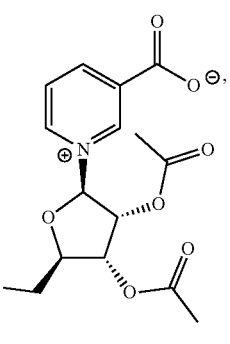
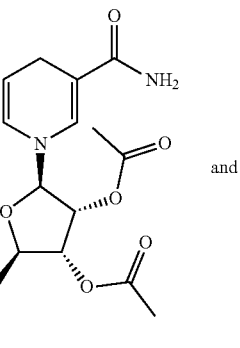
pharmaceutically acceptable salts thereof.
* * * * *

UNITED STATES PATENT AND TRADEMARK OFFICE
CERTIFICATE OF CORRECTION

PATENT NO. : 11,633,421 B2
APPLICATION NO. : 16/464359
DATED : April 25, 2023
INVENTOR(S) : Charles M Brenner et al.

Page 1 of 3

It is certified that error appears in the above-identified patent and that said Letters Patent is hereby corrected as shown below:

In the Claims

Column 37, Lines 3-12, Claim 11, please delete:

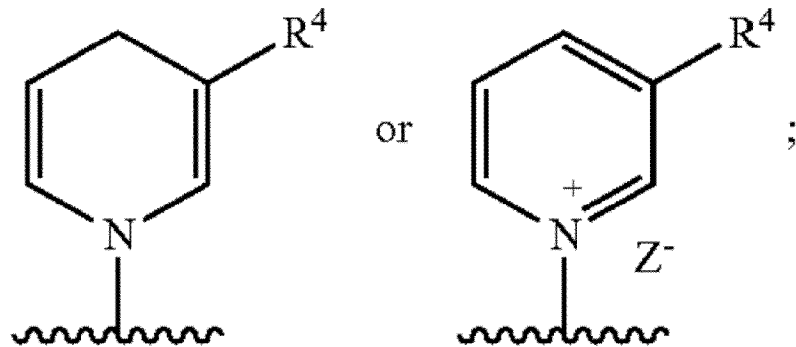

"$A^1$ is                                                                                                 "

And insert:

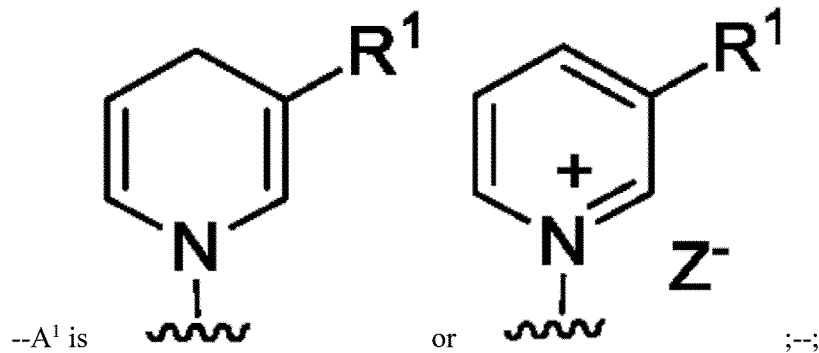

--$A^1$ is              or              ;--;

Signed and Sealed this
Ninth Day of April, 2024

Katherine Kelly Vidal
*Director of the United States Patent and Trademark Office*

CERTIFICATE OF CORRECTION (continued)
U.S. Pat. No. 11,633,421 B2

Column 43, Lines 33-42, Claim 13, please delete:

"A¹ is

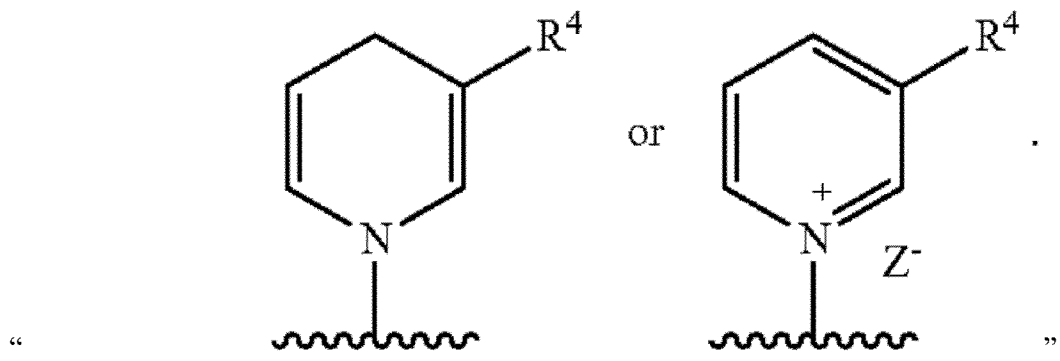

"

And insert:

--A¹ is 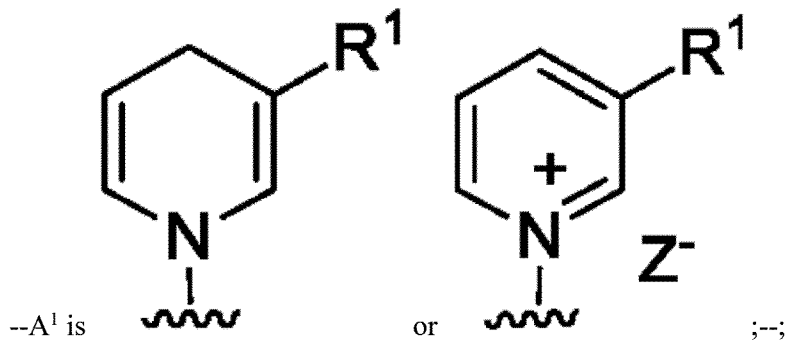 ;--;

CERTIFICATE OF CORRECTION (continued)
U.S. Pat. No. 11,633,421 B2

Column 50, Lines 2-12, Claim 15, please delete:

$A^1$ is

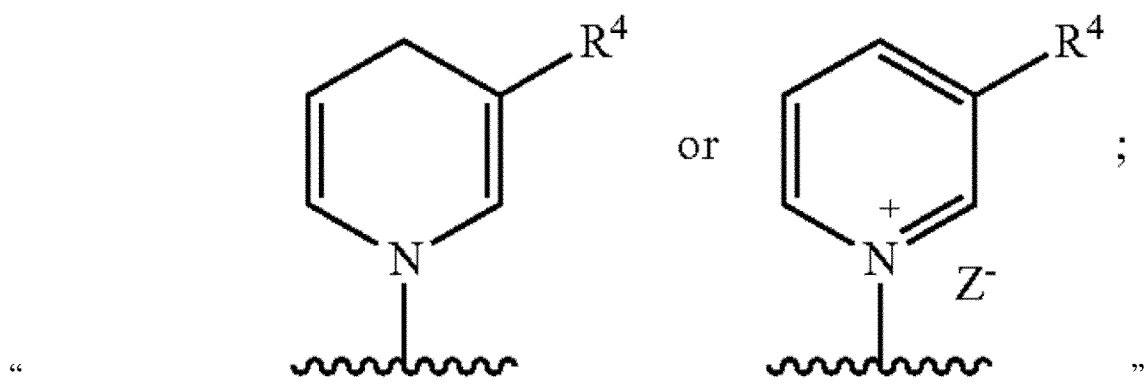

"And insert:

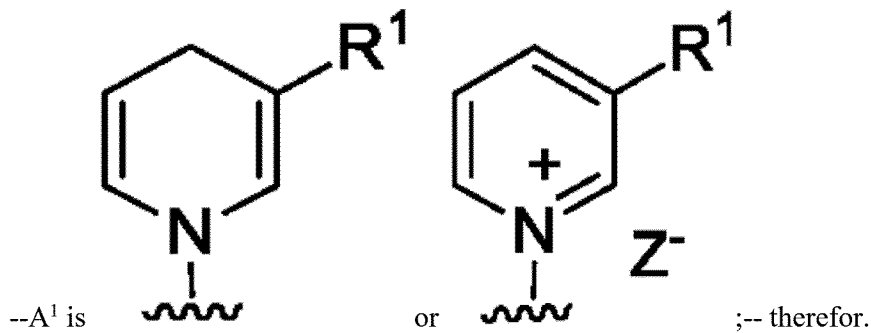

--$A^1$ is ⟿ or ⟿ ;-- therefor.